(12) United States Patent
Nicolai et al.

(10) Patent No.: US 7,238,693 B2
(45) Date of Patent: Jul. 3, 2007

(54) ARYL CARBAMATE DERIVATIVES, PREPARATION AND USE THEREOF

(75) Inventors: Eric Nicolai, Rueil Malmaison (FR); Sophie Curtet, Paris (FR); James Sicsic, Antony (FR); Frank Lezoualc'h, Sevres (FR); Rodolphe Fischmeister, Orsay (FR); Michel Langlois, Sceaux (FR); Magali Maillet, Suresnes (FR); Michèle Launay, Rueil Malmaison (FR)

(73) Assignees: Cerep, Paris (FR); Centre National de la Recherche Scientifique, Paris (FR); Institut National de la Santa et de la Recherche Medicale (inserm), Paris (FR)

( * ) Notice: Subject to any disclaimer, the term of this patent is extended or adjusted under 35 U.S.C. 154(b) by 229 days.

(21) Appl. No.: 10/467,932

(22) PCT Filed: Feb. 22, 2002

(86) PCT No.: PCT/FR02/00668

§ 371 (c)(1),
(2), (4) Date: Aug. 13, 2003

(87) PCT Pub. No.: WO02/068399

PCT Pub. Date: Sep. 6, 2002

(65) Prior Publication Data

US 2004/0058933 A1 Mar. 25, 2004

(30) Foreign Application Priority Data

Feb. 23, 2001 (FR) .................................. 01 02431

(51) Int. Cl.
*A61K 31/501* (2006.01)
*A61K 31/496* (2006.01)
*C07D 401/04* (2006.01)
*C07D 403/04* (2006.01)
*A61K 31/495* (2006.01)
*C07D 295/15* (2006.01)

(52) U.S. Cl. .................... 514/252.02; 514/252.11; 514/252.15; 514/253.01; 514/255.03; 544/238; 544/295; 544/357; 544/360; 544/393

(58) Field of Classification Search ............... 544/238, 544/295, 360; 514/252.02, 252.14, 253.01
See application file for complete search history.

(56) References Cited

U.S. PATENT DOCUMENTS 5,246,935 A * 9/1993 Jeppesen et al. ....... 514/253.05
5,605,896 A 2/1997 Leonardi et al.

FOREIGN PATENT DOCUMENTS

EP 0 199 400 10/1986

| | | |
|---|---|---|
| EP | 0 625 507 | 11/1994 |
| EP | 0 665 216 | 8/1995 |
| EP | 0 903 349 | 3/1999 |
| EP | 0 972 773 | 1/2000 |
| FR | 2 387 955 | 11/1978 |
| WO | WO 93/03725 | 3/1993 |
| WO | WO 93/10742 | 6/1993 |
| WO | WO 93/20071 | 10/1993 |
| WO | WO 95/25100 | 9/1995 |
| WO | WO 95/31449 | 11/1995 |
| WO | WO 99/25687 | 5/1999 |
| WO | WO 00/21926 | 4/2000 |
| WO | WO 00/29377 | 5/2000 |
| WO | WO 00/31032 | 6/2000 |
| WO | WO 00/35449 | 6/2000 |
| WO | WO 00/43391 | 7/2000 |
| WO | WO 01/25199 | 4/2001 |

OTHER PUBLICATIONS

Robichaud et al. in Annual Reports in Medicinal Chemistry, vol. 36, p. 11-20 (2000).*
Database Chemabs, Curtet et al, "Solid-phase synthesis of 2-methoxyaniline derivatives by the traceless silicon linker strategy", & Tetrahedron Lett., 1999, 40(49), 8563-8566.

(Continued)

*Primary Examiner*—Emily Bernhardt
(74) *Attorney, Agent, or Firm*—Nixon & Vanderhye P.C.

(57) ABSTRACT

The present invention relates to novel compounds, the preparation and use, particularly therapeutic, thereof. More specifically, it relates to compounds derived from aryl carbamates, the preparation and use thereof, particularly in the field of human and animal health. The compounds according to the invention are preferably 5-HT$_4$ serotoninergic receptor ligands and can therefore be used in the therapeutic or prophylactic treatment of any disorder involving a 5-HT$_4$ receptor. The invention also relates to pharmaceutical compositions comprising such compounds, the preparation and use thereof and treatment methods using said compounds. Compounds according to the invention include compounds of the following formula (I):

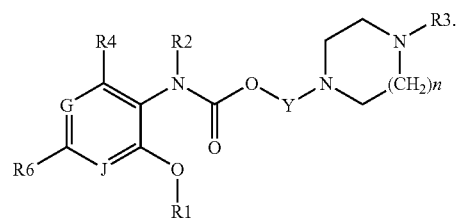

8 Claims, 4 Drawing Sheets

OTHER PUBLICATIONS

Database Chemabs, Soulier et al, "Arylcarbamate Derivatives of 1-Piperidineethanol as Potent Ligands for 5-HT4 Receptors", & J. Med. Chem, 1997, 40(11), 1755-1761.

Database Chemabs, Sedlarova et al, "Studies of physicochemical properties of compounds from the group of 1-(4-phenyl-1-piperazinyl)-3-methoxy-2-propyl 2- and 3-alkoxyphenylcarbamate esters" & Ceska Slov. Farm, 1999, 48(4), 170-174.

Database Chemabs, Hrobonova et al, "Study of local anesthetics. Part 146. Correlation between local anethesia, coded structural information, and chromatographic properties for homologous series of alkoxysubstituted esters of phenylcarbamic acid using a neutral network" & PHARMAZIE, 1999, 54(1), 44-47.

Database Chemabs, Huang et al, "Synthesis and Quantitative Structure-Activity Relationships of N-(1-Benzylpiperidin-4-yl) phenylacetamides and Related Analogs as Potent and Selective .sigma.1 Receptor Ligands" & J. Med. Chem., 1998, 41(13), 2361-2370.

Database Chemabs, Soulier et al, "Arylcarbamate Derivatives of 1-Piperdineethanol as Potent Ligands for 5-HT4 Receptors" & J. Med. Chem., 1997, 40(11), 1755-1761.

Database Chemabs, Cernuskova et al, "3-(4-Phenyl-1-piperazinyl)-2-hydroxy-1-propyl esters of alkoxyphenylcarbamic acids and methods for their preparation" & Farmaceuticka Fakulta UK, Slovakia, Apr. 3, 1996.

Database Chemabs, Cernuskova et al, "3-[4- (2-Methoxyphenyl) -1-piperazinyl] -2-hydroxy-1-propyl esters of alkoxyphenylcarbamic acids and method for their preparation" & Farmaceuticka Fakulta UK, Slovakia, Apr. 3, 1996.

Database Chemabs, Pokorna et al, "Local anesthetics, CXIX. Preparation physicochemical properties and local anesthetic effectiveness of 1,4-bis [2- (2-, 3-, 4-alkoxyphenylcarbamoyloxy) ethyl] -piperazinium dichlorides" & Ceska Slov. Farm, 1996, 45(4), 213-217.

Database Chemabs, Seginko et al, "Ca-antagonistic activity of some 1,4-piperazine derivatives" & PHARMAZIE, 1995, 50(5), 368-9.

DatabaseChemabs, Buciova et al, "Studies of local anesthetics. Part 114. Preparation, local anesthetic and antiarrhythmic effectiveness of 1-(4-methyl-1-piperazinyl)-3-methoxy-2-propyl esters of 2-, 3- and 4- alkoxyphenylcarbamic acids" & Cesk. Farm, 1993, 42(5), 235-8.

Database Chemabs, Sedlarova et al, "Correlation between log k, RM, C and infiltration anesthesia (U) in the group of 4-alkylpiperazinoethyl esters of 2- heptyloxyphenylcarbamic acid" & Cesk. Farm, 1993, 42(2), 92-4.

Database Chemabs, Stankovicova et al, "Study of the relation between physiol-chemical properties and the biological activity of basic heptacaine analogs", PHARMAZIE, 1992, 47(11), 874-5.

Database Chemabs, Do Ngoc Minh et al, "Study of local anesthetics. Part 98. Preparation and local anesthetic activity of 4-alkylpiperazinoethyl esters of o-heptyloxyphenylcarbamic acid" & PHARMAZIE, 1992, 47(2), 94-6.

Database Chemabs, Stankovicova et al, "Kinetics of the alkaline hydrolysis of basic analogs of heptacaine hydrochloride" & PHARMAZIE, 1991, 46(4), 294-5.

Database Chemabs, Stankovicova et al, "Kinetics of alkaline hydrolysis of hepatacaine chloride basic analogs" & Chem Pap., 1990, 44(2), 171-6.

Database Chemabs, Csollei et al, "Studies of local anesthetics. LXXXV. N-Alkyl-4-piperidyl esters of o- and m-alkoxycarbanilic acids with local anesthetic and antiarrhythmic effects", & Cesk. Farm, 1986, 35(7), 299-302.

Database Chemabs, Dubey et al, "Derivatives of N-aryl-N-aminopiperazines as potential cardiovascular agents" & Pol. J. Pharmacol. Pharm, 1981, 33(3), 349-57.

Database Chemabs, Ahmad et al, "Piperazinylthioureas and thiozolidones as anthelminitcs" & Proc. Natl. Acad. Sci., India, Sect. A, 1980, 50(3), 163-8.

Database Chemabs, Csollei, "N-butyl-3-pyrrolidinyl- and N-ethyl-2-pyrrolidinylmethyl esters of alkoxycarbanilic acids with local anesthetic effects" & Farm. Obz, 1981, 50(8), 407-11.

Database Chemabs, Chaturvedi et al, Anticonvulsant activity of N,N'-bis[3-(3-substituted ures) propyl] piperazines J. Pharm. Sci, 1975, 64(3), 454-6.

Database Chemabs, Chaturvedi et al, "Piperazinothioureas as anticonvulsants" & Curr. Sci., 1972, 41(7), 253-4.

Database Chemabs, Mager et al, "Multivariate Free-Wilson analysis" & PHARMAZIE, 1981, 36(6), 427-9.

Database Chemabs, Gupta et al, "Synthesis of substituted piperidino carbamaides. Correlation between CNS [central nervous system] effects and selective inhibition of NAD-dependent oxidations" & J. Pharm. Sci., 1974, 63(8), 1227-30.

* cited by examiner

ARYL CARBAMATE DERIVATIVES, PREPARATION AND USE THEREOF

This application is the U.S. national phase of international application PCT/FR02/00668 filed 22 Feb. 2002 which designated the U.S.

The present invention relates to novel compounds, the preparation and use, particularly therapeutic, thereof. More specifically, it relates to compounds derived from aryl carbamates, the preparation and use thereof, particularly in the field of human and animal health. The compounds according to the invention are preferably 5-$HT_4$ serotoninergic receptor ligands and can therefore be used in the therapeutic or prophylactic treatment of any disorder involving a 5-$HT_4$ receptor. The invention also relates to pharmaceutical compositions comprising such compounds, the preparation and use thereof and treatment methods using said compounds.

A large number of serotonin-dependent processes have been identified to date, and many molecules acting at serotonin receptors are used in human therapeutics. More than a dozen serotonin receptors have been identified, one of the most recent being the 5-$HT_4$ receptor (J. Bockaert et al., Trends Pharmacol. Sci., 13, 141, 1992). The present invention relates to aryl carbamate derivatives represented by the general formula (I) and their pharmacologically acceptable salts. They are preferably compounds capable of interfering with serotonin-dependent processes, even more preferably 5-$HT_4$ receptor ligands, particularly the human serotype thereof. The invention thus discloses methods of treatment or prophylaxis of any disorder involving a 5-$HT_4$ receptor. The compounds and compositions according to the invention may be proved useful in the therapeutic or prophylactic treatment of different pathologies such as

- various gastrointestinal disorders such as gastroesophageal reflux disease (GERD), irritable bowel syndrome, functional dyspepsia, gastroparesis, disorders linked to intestinal motility, nausea, and constipation,
- central nervous system disorders such as anxiety, pain, schizophrenia, depression, memory impairment and dementia,
- cardiac disorders such as atrial fibrillation, arrhythmia and tachycardia,
- urologic disorders such as urinary retention, incontinence.

A first object of the invention is based on compounds represented by the general formula (I):

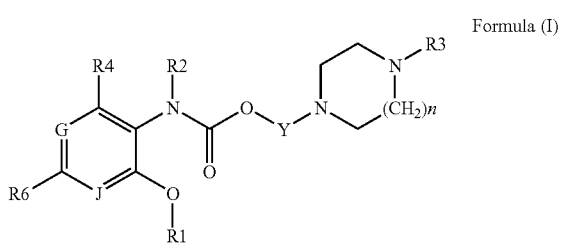

Formula (I)

wherein:
$R_1$ represents a lower alkyl or a lower arylalkyl group,
$R_2$ represents a hydrogen atom or a lower alkyl group,
$R_3$ represents an aryl group or a heterocycle, chosen from among phenyl, naphthyl, thienyl, furyl, pyridyl, pyrimidinyl, pyridazinyl, pyrazinyl, such group possibly being substituted by one or more groups chosen from among halogeno, alkoxy, cyano, hydroxy, nitro, alkyl, halogenoalkyl, alkylthio, —$NHR_8$, —$NHCOR_8$, —$NHSO_2R_8$, —$NHCONR_8R_9$ Y represents a linear or branched alkylene chain or bond, containing 2 to 5 carbon atoms,
J represents a C—$R_7$ group or the nitrogen atom,
G represents a C—$R_5$ group or the nitrogen atom,
$R_4$, $R_5$, $R_6$ and $R_7$ taken individually represent the hydrogen atom, a halogen atom, a lower alkyl group, an alkoxy, alkylthio, alkylsulfonyl, alkylsulfoxide, trifluoromethyl, nitro, cyano, carboxy, carboxyalkyl, alkylamino or dialkylamino group,
$R_8$ and $R_9$ represent the hydrogen atom, an aryl group or a lower alkyl group,
or, when G or J are not the nitrogen atom, the groups $OR_1$ and $R_7$ and/or the groups $R_6$ and $R_7$ and/or the groups $R_6$ and $R_5$ and/or the groups $R_5$ and $R_4$ may form, together with the aromatic ring to which they are attached, a saturated or unsaturated ring,
n is equal to 1 or 2, said alkyl, alkylene, aryl, arylalkyl, heterocycle and carboxyalkyl groups, and the ring, being substituted or not, with the exception of compounds represented by formula (I) wherein:
Y represents a 1-(methoxymethyl)ethyl or 2-hydroxypropyl group, $R_3$ represents a phenyl or 2-methoxyphenyl group, when $R_1$ represents a lower alkyl group, $R_2$, $R_4$ and $R_6$ represent a hydrogen atom, G and J represent a CH group and n is equal to 1,
and the salts thereof.

According to the present invention, the term "lower alkyl" more specifically denotes a linear or branched hydrocarbon group having from 1 to 6 carbon atoms such as methyl, ethyl, propyl, isopropyl, butyl, isobutyl, tert-butyl, pentyl, neopentyl, n-hexyl. $C_1$–$C_4$ groups are preferred. Methyl and ethyl groups are especially preferred.

"Aryl" groups are mono-, bi- or tri-cyclic aromatic hydrocarbon systems having from 6 to 18 carbon atoms. The phenyl and naphthyl groups are specific examples.

"Alkylene" groups in the context of the invention are divalent groups corresponding to the alkyl groups defined hereinabove in which a hydrogen atom has been removed.

"Alkoxy" groups correspond to the alkyl groups defined hereinabove bonded to the ring by means of an —O— (ether) bond.

"Alkylthio" groups correspond to the alkyl groups defined hereinabove bonded to the ring by means of an —S— (thioether) bond.

"Halogen" denotes a fluorine, chlorine, bromine or iodine atom.

"Halogenoalkyl" denotes an alkyl group such as defined hereinabove in which one or more hydrogen atoms have been replaced by one or more halogen atoms. The trifluoromethyl function is a specific example.

"Heteroatom" denotes an atom chosen from among N, O and S.

Arylalkyl groups are groups comprising an aryl function as defined hereinabove bonded to the ring by means of an alkylene chain.

When the $OR_1$ and $R_7$ groups and/or the $R_6$ and $R_7$ groups and/or the $R_6$ and $R_5$ groups and/or the $R_5$ and $R_4$ form, together with the aromatic ring to which they are attached, a saturated or unsaturated ring, it is preferably a ring comprising from 3 to 8 atoms, aromatic or not, possibly containing one or more heteroatoms, preferably 0 to 3. Preferred examples of such rings include in particular benzofuran, dihydrobenzofuran, benzodioxane, benzopyran, dihydrobenzopyran, benzodioxole.

Furthermore, as indicated hereinabove, these different groups may or may not contain one or more substituents, chosen for example from among halogen, nitro, cyano, trifluoromethyl, carboxy, (C1–C6)-alkoxycarbonyl, mono- or di-($C_1$–$C_6$)-alkylaminocarbonyl, aminocarbonyl, mono- or di-(C6–C12)-aryl- or hetero-($C_2$–$C_{12}$)-arylaminocarbonyl, mono- or di-($C_6$–$C_{12}$)-aryl- or hetero-($C_2$–$C_{12}$)-aryl-($C_1$–$C_6$)-alkylaminocarbonyl, hydroxy, alkoxy, ($C_1$–$C_6$)-alkyl, amino possibly substituted by one or more groups chosen from among ($C_1$–$C_6$)-alkyl, ($C_3$–$C_8$)-cycloalkyl, ($C_2$–$C_{12}$)-aryl, hetero-($C_2$–$C_{12}$)-aryl, ($C_6$–$C_{12}$)-aryl-($C_1$–$C_6$)-alkyl, hetero-($C_2$–$C_{12}$)-aryl-($C_1$–$C_6$)-alkyl, ($C_1$–$C_7$)-alkanoyl, cyclo-($C_3$–$C_8$)-alkanoyl($C_6$–$C_{12}$)-aroyl, or ($C_6$–Cl 2)-aryl-($C_1$–$C_7$)-alkanoyl.

The compounds of the present invention display excellent selectivity for the 5-$HT_4$ receptor as compared to other 5-HT receptor subtypes and particularly as compared to the 5-$HT_3$ receptor. For instance, the compound 2-[4-(4-pyridinyl)piperazino]ethyl-N-(2-methoxyphenyl) carbamate (63) has a Ki of 5 nM for the 5-$HT_4$ receptor and no activity up to a concentration of 1 µM for the 5-$HT_{1A}$, 5-$HT_{1B}$, 5-$HT_{2A}$, 5-$HT_{2C}$, 5-$HT_3$, 5-$HT_{5A}$, 5-$HT_6$ or 5-$HT_7$ receptors.

Furthermore, in an advantageous manner, the compounds of the present invention, in contrast to other known 5-$HT_4$ or 5-$HT_3$ ligands like Cisapride, do not have side effects such as serious cardiovascular complications.

Preferred compounds of the invention are compounds represented by formula (I) hereinabove wherein:

$R_1$ represents a methyl or ethyl group, and/or $R_3$ represents an aryl group or a heterocycle having 6 atoms, possibly substituted, preferably containing one or two nitrogen atoms, or a phenyl group possibly substituted, and/or n=1 and/or Y is an alkylene chain of 2 or 3 carbon atoms, preferably linear, and/or $R_2$ is a hydrogen atom, and/or $R_4$ is a hydrogen atom, and/or $R_6$ is a hydrogen atom, and/or G is a CH group, and/or J is a CH group.

A preferred subfamily according to the invention is represented by compounds having formula (I) wherein $R_1$ is a methyl or ethyl group. As illustrated in the examples, such derivatives according to the invention display advantageous properties as 5-$HT_4$ receptor ligands.

An especially preferred family is that in which $R_1$ represents a methyl or ethyl group.

Another particular category of compounds according to the invention is represented by compounds having the general formula (I) wherein $R_3$ represents a heterocycle of 6 atoms, possibly substituted, containing one or two nitrogen atoms or a phenyl group, possibly substituted.

According to an especially preferred variant, the invention has as its object compounds represented by formula (I) wherein $R_1$ is a methyl or ethyl group and $R_3$ represents a phenyl group possibly substituted.

According to another especially preferred variant, the invention has as its object compounds represented by formula (I) wherein $R_1$ is a methyl or ethyl group and $R_3$ is a heterocycle of 6 atoms, possibly substituted, containing one or two nitrogen atoms.

A specific family according to the invention comprises compounds represented by general formula (I) such as defined hereinabove, and the subfamilies indicated hereinabove, wherein $R_2$ is a hydrogen atom, and/or $R_4$ is a hydrogen atom, and/or $R_6$ is a hydrogen atom, wherein even more preferably at least two of the groups $R_2$, $R_4$ and $R_6$ are a hydrogen atom, even more preferably wherein the three groups $R_2$, $R_4$ and $R_6$ each represent a hydrogen atom.

Another specific family according to the invention comprises compounds represented by general formula (I) such as defined hereinabove, and the subfamilies indicated hereinabove, wherein G is the CH group and/or J is the CH group, more preferably wherein G and J each represent a CH group.

A further specific family according to the invention comprises compounds represented by general formula (I) such as defined hereinabove, and the subfamilies indicated hereinabove, wherein n is equal to 1.

Another specific family according to the invention comprises compounds represented by general formula (I) such as defined hereinabove, and the subfamilies indicated hereinabove, wherein Y is an alkylene chain containing 2 or 3 carbon atoms, preferably not branched.

As noted, the compounds of the invention may be in the form of salts, particularly acid or base salts, preferably compatible with pharmaceutical use.

Non-limiting examples of pharmaceutically acceptable acids include hydrochloric, hydrobromic, sulfuric, phosphoric, acetic, trifluoroacetic, lactic, pyruvic, malonic, succinic, glutaric, fumaric, tartaric, maleic, citric, ascorbic, methane or ethanesulfonic, camphoric acids, etc. Non-limiting examples of pharmaceutically acceptable bases include sodium hydroxide, potassium hydroxide, triethylamine and tert-butylamine.

Specific examples of preferred compounds according to the invention are the following compounds in particular:

2-[4-(3-methoxyphenyl)piperazino]ethyl-N-(2-ethoxyphenyl)carbamate 15

2-[4-(3-methylphenyl)piperazino]ethyl-N-(2-ethoxyphenyl)carbamate 21

2-[4-(2-pyridinyl)piperazino]ethyl-N-(2-ethoxyphenyl)carbamate 24

2-[4-(3-pyridazinyl)piperazino]ethyl-N-(2-ethoxyphenyl)carbamate 25

3-[4-(4-fluorophenyl)piperazino]propyl-N-(2-ethoxyphenyl)carbamate 38

3-[4-(2-pyridinyl)piperazino]propyl-N-(2-ethoxyphenyl)carbamate 40

3-[4-(4-pyridinyl)piperazino]propyl-N-(2-ethoxyphenyl)carbamate 41

3-[4-(3-pyridazinyl)piperazino]propyl-N-(2-ethoxyphenyl)carbamate 42

3-[4-(4-pyrimidinyl)piperazino]propyl-N-(2-ethoxyphenyl)carbamate 43

3-[4-(2-pyrimidinyl)piperazino]propyl-N-(2-ethoxyphenyl)carbamate 44

3-[4-(6-methyl-3-pyridazinyl)piperazino]propyl-N-(2-ethoxyphenyl)carbamate 48

2-(4-phenylpiperazino)ethyl-N-(2-methoxyphenyl)carbamate 49

2-[4-(3-methoxyphenyl)piperazino]ethyl-N-(2-methoxyphenyl)carbamate 51

2-[4-(2-pyridinyl)piperazino]ethyl-N-(2-methoxyphenyl)carbamate 62

2-[4-(3-pyridazinyl)piperazino]ethyl-N-(2-methoxyphenyl)carbamate 64

2-[4-(2-pyrimidinyl)piperazino]ethyl-N-(2-methoxyphenyl)carbamate 65

3-[4-(4-pyridinyl)piperazino]propyl-N-(2-methoxyphenyl)carbamate 83 such as described in the examples, and the salts thereof, particularly compounds 15, 24, 25, 38,40,41,49.

Compounds represented by formula (I) may be prepared by methods known to those skilled in the art. In this regard, the present invention describes different synthetic routes, illustrated in FIGS. 1–5 and in the examples, and which may be utilized by those skilled in the art, as indicated in the examples. The starting compounds may be obtained commercially or synthesized by the usual methods. It is understood that the present application is not restricted to a particular route of synthesis, and encompasses other methods by which to produce the indicated compounds. As an example, the compounds represented by formula (I) may be synthesized either in liquid phase as depicted in illustrations 1–4 (FIGS. 1–4) or by parallel synthesis on a solid support according to illustration 5 (FIG. 5).

According to a particular object, the invention is based on a method for preparing a compound such as defined hereinabove, wherein a product represented by formula (II) is reacted with a product represented by formula (III):

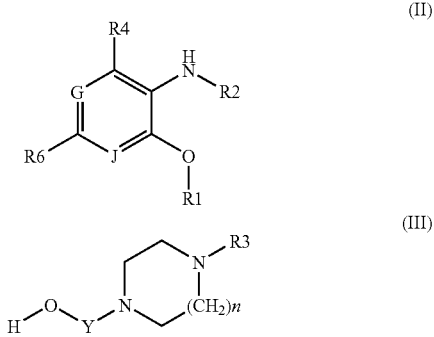

in which the groups $R_1$, $R_2$, $R_3$, $R_4$, $R_6$, Y, J, G and n are defined as hereinabove, in the presence of a carbonyl donor reagent, preferably the $(Boc)_2O/DMAP$ system, and the resulting product is recovered. The reaction is advantageously carried out in a solvent, for example neutral, typically an aprotic solvent (see FIG. 1).

Another particular object of the invention is a method for preparing a compound such as defined hereinabove, wherein a product represented by formula (II) is reacted with a product represented by formula (III) in which the groups $R_1$, $R_2$, $R_3$, $R_4$, $R_6$, Y, J, G and n are defined as hereinabove, in a $CXCl_2$/pyridine system, and the resulting product is recovered. The reaction is advantageously carried out in a solvent, for example neutral, typically an aprotic solvent (see FIG. 2).

A further specific object of the invention is a method for preparing a compound such as defined hereinabove, wherein a product represented by formula (II) is reacted with a product represented by formula (XVI) and a product represented by formula (XVII), in which the groups $R_1$, $R_2$, $R_3$, $R_4$, $R_6$, Y, J, G and n are defined as hereinabove, and the resulting product is recovered. The reaction is advantageously carried out in the presence of $Et_2O$ (see FIG. 3).

An additional specific object of the invention is a method for preparing a compound such as defined hereinabove, wherein a product represented by formula (II) is reacted with a product represented by formula (XVIII) in which the groups $R_1$, $R_2$, $R_3$, $R_4$, $R_6$, Y, J, G and n are defined as hereinabove, and the resulting product is recovered. The reaction is advantageously carried out in a solvent, for example $CH_3CN$ or dioxane (see FIG. 4).

According to another variant, the invention relates to a method for preparing a compound such as described hereinabove, wherein a product represented by formula (XIV) is reacted with a product represented by formula (XII):

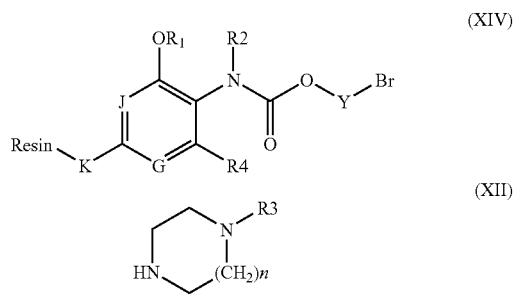

in which the groups $R_1$, $R_2$, $R_3$, $R_4$, Y, J, G and n are defined as hereinabove and K is a spacer group, in the presence of DIEA, and wherein the resulting product is released by chemical cleavage.

More specifically, the spacer group K has the following formula (XV):

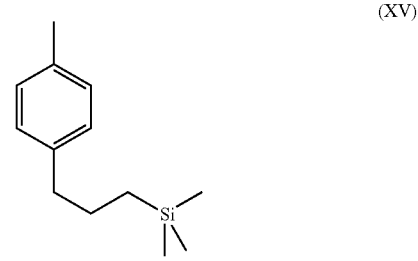

the product then having the structure of the compound represented by formula (XI).

Moreover, the method advantageously comprises preparing the compound represented by formula (XIV) [or formula (XI)] according to the reaction route shown in FIG. 5.

Another object of the present invention relates to any pharmaceutical composition comprising a compound such as defined hereinabove. Such pharmaceutical composition is advantageously for the treatment or prophylaxis of diseases involving a 5-$HT_4$ receptor, for example the 5-$HT_{4e}$ receptor. The pharmaceutical compositions according to the invention may be used in particular for the treatment or prophylaxis of gastrointestinal disorders, central nervous system disorders, cardiac disorders or urologic disorders.

The invention equally relates to the use of a compound such as defined hereinabove for preparing a pharmaceutical composition for implementing a method of treatment or prophylaxis in the human or animal body.

The invention further concerns a method for treating a disease involving a 5-$HT_4$ receptor, comprising administering to a subject, particularly human, an effective dose of a compound or a pharmaceutical composition such as defined hereinabove.

The pharmaceutical compositions of the invention advantageously contain one or more pharmaceutically acceptable excipients or vehicles. These may be exemplified by saline, physiological, isotonic, buffered solutions, etc., compatible with pharmaceutical use and known to those skilled in the art. The compositions may contain one or more agents or vehicles chosen from among dispersives, solubilizers, stabilizers, preservatives, and the like. Agents or vehicles that may be used in the formulations (liquids and/or injectables and/or solids) comprise in particular methylcellulose, hydroxymethylcellulose, carboxymethylcellulose, polysorbate 80, mannitol, gelatine, lactose, vegetable oil, acacia, and the like. The compositions may be formulated as a suspension for injection, gels, oils, tablets, suppositories, powders, capsules, gelules, and the like, possibly by means of pharmaceutical forms or devices allowing sustained and/or delayed release. For this type of formulation, an agent such as cellulose, carbonates or starches is advantageously used.

The compounds or compositions according to the invention may be administered in various ways and in different forms. For instance, they may be injected by the systemic route or given orally, preferably by the systemic route, such as for example by the intravenous, intramuscular, subcutaneous, transdermal, intra-arterial route, etc. For injections, the compounds are generally prepared as liquid suspensions, which may be injected through syringes or by infusion, for instance. It is understood that the rate and/or injected dose may be adapted by those skilled in the art according to the patient, the pathology, the method of administration, etc. Typically, the compounds are administered at doses ranging from 0.1 μg to 100 mg/kg of body weight, more generally from 0.01 to 10 mg/kg, typically between 0.1 and 10 mg/kg. Furthermore, repeated injections may be given, as the case may be. Moreover, the compositions according to the invention may additionally comprise other active substances or agents.

Other aspects and advantages of the present invention will become apparent in the following examples, which are given for purposes of illustration and not by way of limitation.

MATERIALS AND METHODS

Figure 1:
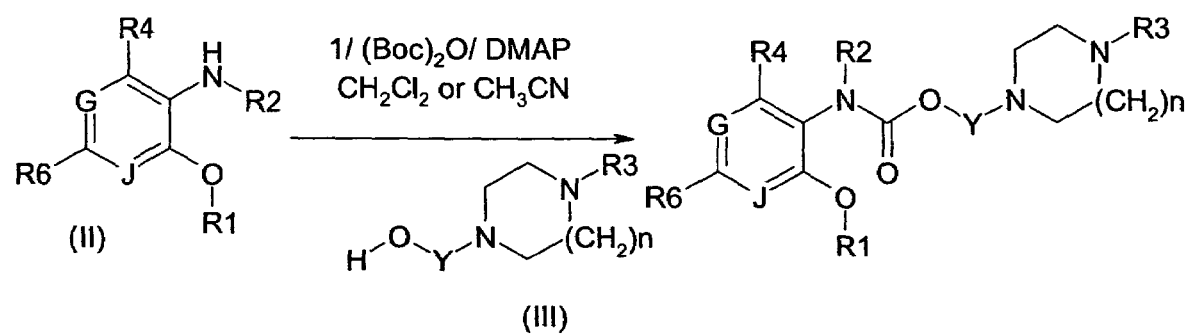
FIG. 1: Route of synthesis 1 of compounds according to the invention. Y, G, J and groups $R_1$–$R_9$ are defined as hereinabove.
Figure 2:
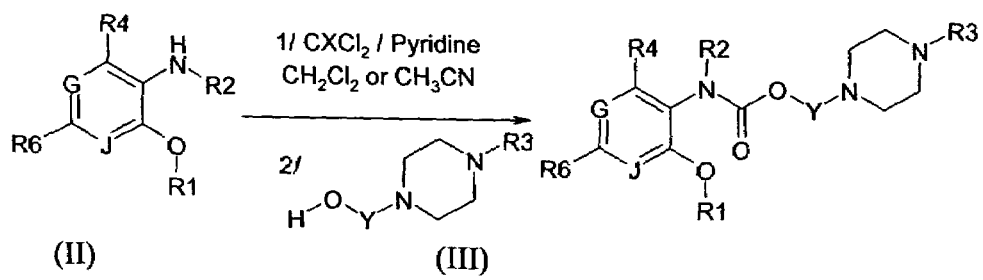
FIG. 2: Route of synthesis 2 of compounds according to the invention. Y, G, J and groups $R_1$–$R_9$ are defined as hereinabove.
Figure 3:
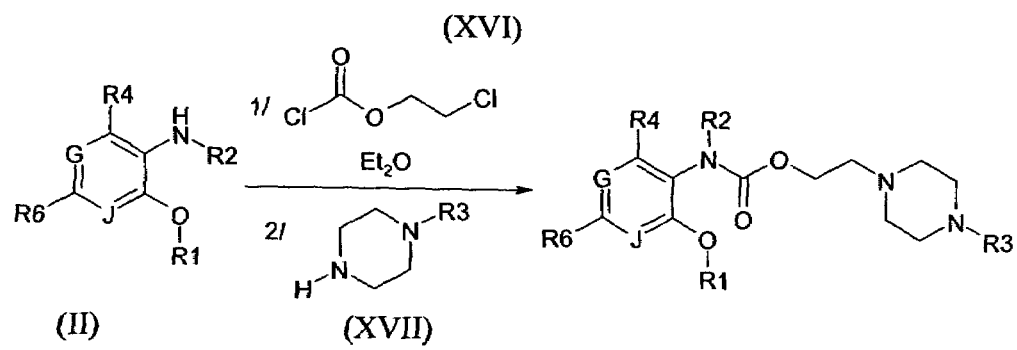
FIG. 3: Route of synthesis 3 of compounds according to the invention. Y, G, J and groups $R_1$–$R_9$ are defined as hereinabove.
Figure 4:
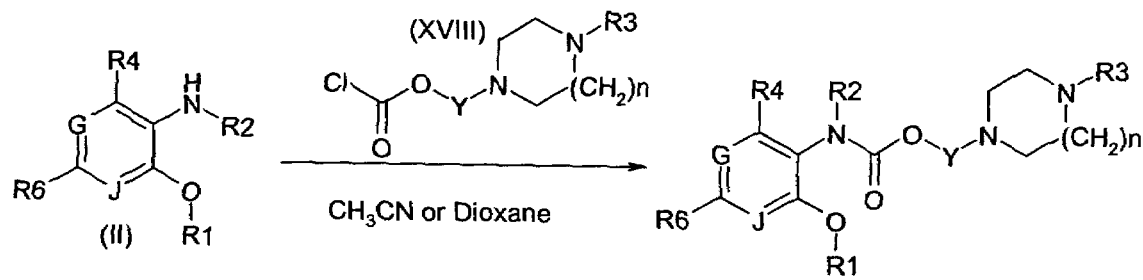
FIG. 4: Route of synthesis 4 of compounds according to the invention. Y, G, J and groups $R_1$–$R_9$ are defined as hereinabove.
Figure 5:
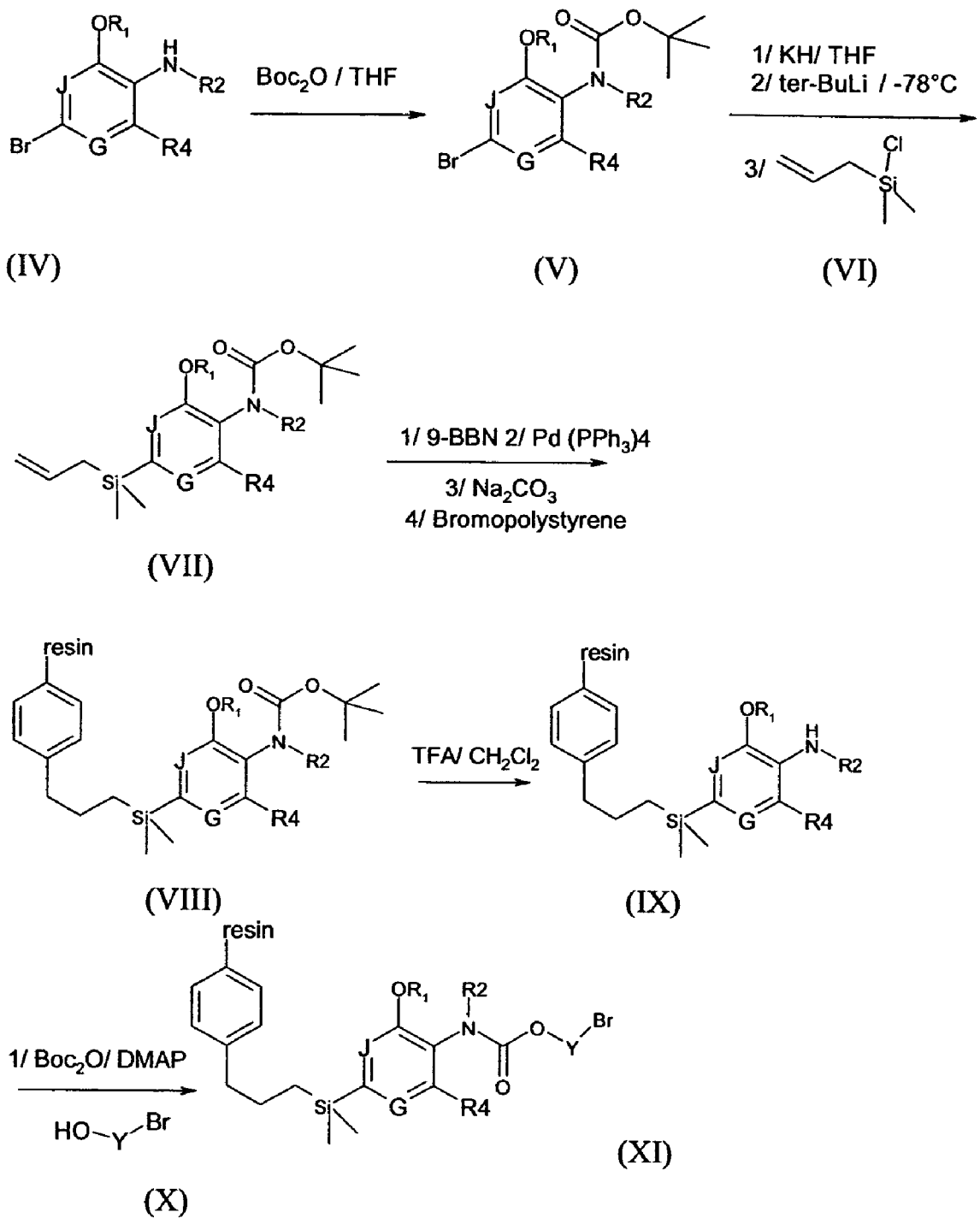
FIG. 5: Route of synthesis 5 of compounds according to the invention. Y, G, J and groups $R_1$–$R_9$ are defined as hereinabove.
Figure 5:
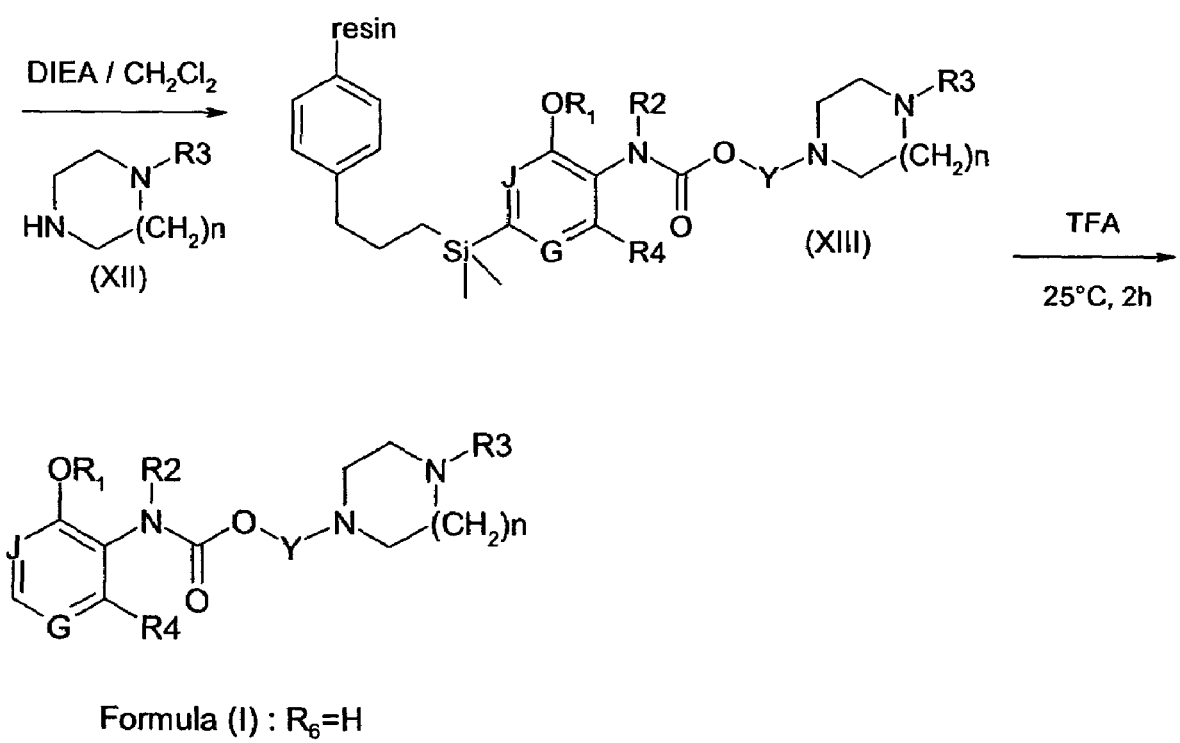

The compounds of the invention were obtained through classic methods of parallel synthesis and organic synthesis.

The $^1$H and $^{13}$C NMR spectra were recoded on a Brucker AC-200 spectrometer. Chemical shifts are given in ppm with tetramethylsilane as internal reference. The symbols m, s, sl, d, t, q, quint., dd, td, etc. respectively denote multiplet, singlet, wide singlet, doublet, triplet, quadruplet, quintuplet, split doublet, split triplet. Infrared spectra were recorded on a Perkin Elmer 841 instrument as KBR disks or on a Brucker vector 22 Fourier transform instrument.

Melting points were determined in a Kofler apparatus. HPLC spectra were recorded on a Shimadzu SCL10A with a Uptisphere UP50 DB-5m C18 column (4.6×50 mm) at a flow rate of 4 ml/min and a wavelength of 220 nm. HPLC/MS analyses were carried out on a LC Micromass Plateform spectrometer (TSK gel super ODS column, 4.6 mm ID×5 cm, flow rate 2.75 ml/min, gradient: 100% A to 100% B in 3 min, 1 min plateau at 100% B; solvent A=water/0.05% trifluoroacetic acid, solvent B=acetonitrile/water/trifluoroacetic acid (80:20:0.05).

Unless otherwise indicated, the products used to prepare compounds represented by formula (I) were obtained commercially and used without out further purification. The experimental protocols described below are given for purposes of illustration and not at all by way of limitation. Unless otherwise indicated, percentages are expressed on a weight basis.

EXAMPLE 1

4-bromo-2-methoxyaniline 2

At room temperature, 3.4 ml (30 mmol, 1.25 eq) of 2-methoxyaniline is diluted in 10 ml of acetic acid. Over approximately 1 hour, 1.2 ml (24 mmol, 0.8 eq) of bromine dissolved in 10 ml of acetic acid is added dropwise. A purple precipitate is formed. When all the bromine has been added, the hydrobromide is filtered on a Buchner funnel and rinsed with acetic acid. Take up the solid in a $H_2O/CH_2Cl_2$ mixture. A slight excess of KOH pellets is added, the aqueous phase is extracted with $CH_2Cl_2$ and the organic phase is dried on $MgSO_4$. Concentration under reduced pressure gives a brown oil which is purified by column chromatography (eluent $CH_2Cl_2$). The expected product (3.46 g) is a colorless oil (yield: 57%).

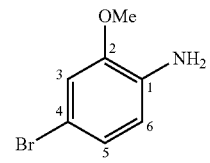

$C_7H_8BrNO$ M=202.06 g/mol $^1$H NMR (CDCl$_3$) δ (ppm): 6.89 (dd, $J_o$=8.7 Hz, $J_m$=2.03 Hz, 1H, CH$_{(5)}$); 6.87 (sl, 1H, CH$_{(3)}$); 6.57 (dd, $J_o$=8.7 Hz, $J_p$=1.96 Hz, 1H, CH$_{(6)}$); 3.83 (s, 3H, OCH$_3$); 3.76 (sl, 2H, NH$_2$). $^{13}$C NMR (CDCl$_3$) δ (ppm): 147.9 (C$_2$); 135.6 (C$_1$); 123.7 (C$_5$); 115.8 (C$_6$); 113.7 (C$_3$); 109.4 (C$_4$); 55.7 (OCH$_3$).

| | Elemental analysis: | |
| --- | --- | --- |
| | Calc. | Exp. |
| % C | 41.61 | 41.48 |
| % H | 3.99 | 3.90 |
| % N | 6.93 | 6.85 |

EXAMPLE 2 tert-butyl-N-(4-bromo-2-methoxyphenyl)carbamate 4

In a 250 ml single-necked flask placed under an inert atmosphere, 6.4 g (31.7 mmol) of 4-bromo-2-methoxyaniline 2 and 7.6 g (34.9 mmol, 1.1 eq) of $(Boc)_2O$ are dissolved in 80 ml of anhydrous THF. Heat the THF under a reflux condenser for 15 hours. The medium is allowed to cool and the solvent is evaporated. The residue is taken up in $CH_2Cl_2$, washed with a saturated aqueous solution of $NaHCO_3$ (3×). The organic phase is dried on $MgSO_4$. A concentration under vacuum is implemented to produce a brown oil which is purified by column chromatography (eluent petroleum ether/AcOEt 9:1). 9.6 g of 4 is obtained as a colorless oil (yield: 100%).

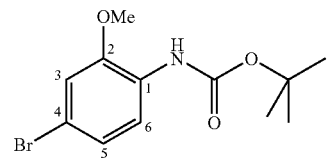

$C_{12}H_{16}BrNO_3$ $M=302.19$ g/mol $^1H$ NMR $(CDCl_3)$ δ (ppm): 7.95 (d, J=8.6 Hz, 1H, $CH_{(6)}$); 7.07–6.94 (m, 3H, NH, $CH_{(3)}$, $CH_{(5)}$); 3.84 (s, 3H, $OCH_3$); 1.52 (s, 9H, $CH_3$). $^{13}C$ NMR $(CDCl_3)$ δ (ppm): 152.5 $(CO_2)$; 148.1 $(C_2)$; 127.4 $(C_1)$; 123.8 $(C_5)$; 119.1 $(C_6)$; 114.3 $(C_4)$; 113.4 $(C_3)$; 80.5 ($\underline{C}(CH_3)_3$); 55.9 $(O\underline{C}H_3)$; 28.3 (3C, $\underline{C}H_3$).

EXAMPLE 3 tert-butyl-N-{4-[allyl(dimethyl)silyl]-2-methoxyphenyl}carbamate 6

To 2.4 g (20.6 mmol, 1.2 eq) of 35% potassium hydride suspended in 70 ml of anhydrous THF under an argon atmosphere, at room temperature 5.2 g (17.2 mmol) of tert-butyl-N-(4-bromo-2-methoxyphenyl)carbamate 4 diluted in 60 ml of anhydrous THF is added dropwise. This mixture is shaken for 10 min before cooling to −78° C. When this temperature is reached, 23.5 ml (35.3 mmol, 2.05 eq) of 1.5 M tert-butyllithium is added through a cannula in hexane diluted in 50 ml of anhydrous THF and previously cooled to −78° C. The reaction is allowed to progress for 20 min at −78° C. before adding 6.2 ml (41.3 mmol, 2.4 eq) of allyl(chloro)dimethylsilane all at once. The temperature is allowed to rise to −10° C. then the medium is hydrolyzed with a small amount of water. Next, 90 ml of AcOEt is added and the organic phase is washed with $H_2O$ (3×90 ml), 1 M $NaHSO_4$ (2×90 ml), then a saturated aqueous solution of NaCl (1×90 ml), and lastly, dried on $MgSO_4$. Concentration under vacuum gives an orange oil which is purified by column chromatography (eluent petroleum ether/AcOEt 9:1), producing 4.28 g of a colorless oil (yield: 77%).

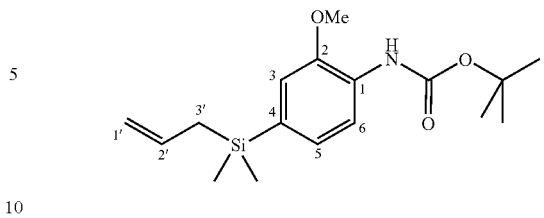

$C_{17}H_{27}NO_3Si$ M=321.47 g/mol $^1H$ NMR $(CDCl_3)$ δ (ppm): 8.05 (d, J=8 Hz, 1H, $CH_{(6)}$); 7.12 (sl, 1H, NH); 7.08 (dd, J=8 Hz, J=1.2 Hz, 1H, $CH_{(5)}$); 6.94 (d, J=1.2 Hz, 1H, $CH_{(3)}$); 5.78 (ddt, J=16.9 Hz, J=10.1 Hz, J=8.1 Hz, 1H, $CH_{(2')}$); 4.86 (m, 2H, $CH_{2(1')}$); 3.88 (s, 3H, $OCH_3$); 1.74 (dt, J=8.1 Hz, J=1.2 Hz, 2H, $CH_2Si$); 1.52 (s, 9H, $CH_3$); 0.26 (s, 6H, $(CH_3)_2Si$). $^{13}C$ NMR $(CDCl_3)$ δ (ppm): 152.6 $(CO_2)$; 146.9 $(C_2)$; 134.7 $(C_{2'})$; 131.7 $(C_4)$; 128.9 $(C_1)$; 126.7 $(C_5)$; 117.4 $(C_6)$; 114.3 $(C_3)$; 113.2 $(C_{1'})$; 80.3 ($\underline{C}(CH_3)_3$); 55.5 (O$\underline{C}H_3$) 28.8 (3C, $\underline{C}H_3$); 23.8 $(C_{3'})$; −3.4 (2C, $\underline{C}H_3Si$).

EXAMPLE 4

4-bromo-2-ethoxyaniline 3

Over approximately 1 hour, 3 ml (58.4 mmol) of bromine dissolved in 20 ml of acetic acid is added dropwise to 7.8 ml (60 mmol, 1.03 eq) of 2-ethoxyaniline diluted in 20 ml of acetic acid. When all the bromine has been added, the precipitate formed is filtered on a Buchner funnel and rinsed with acetic acid. The hydrobromide is taken up in $H_2O$, 5 g (90 mmol, 1.5 eq) of KOH pellets is added and extracted with $CH_2Cl_2$. The organic phase is dried on $MgSO_4$ and the solvent is evaporated. The residue is purified by column chromatography (eluent $CH_2Cl_2$/pentane 9:1) to produce 7.52 g of the expected product as a brown oil (yield: 58%).

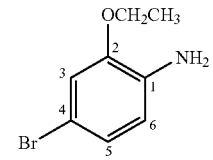

$C_8H_{10}BrNO$ M=216.09 g/mol $^1H$ NMR $(CDCl_3)$ δ (ppm): 6.89 (dd, $J_o$=8.6 Hz, $J_m$=2 Hz, 1H, $CH_{(5)}$); 6.87 (sl, 1H, $CH_{(3)}$); 6.57 (dd, $J_o$=8.6 Hz, $J_p$=2 Hz, 1H, $CH_{(6)}$); 4.02 (q, J=7 Hz, 2H, $CH_2O$); 3.56 (sl, 2H, $NH_2$); 1.43 (t, J=7 Hz, 3H, $CH_3$).

EXAMPLE 5 tert-butyl(N-(4-bromo-2-ethoxyphenyl)carbamate 5

The reaction between 7.2 g (33.3 mmol) of 4-bromo-2-ethoxyaniline 3 and 8 g (36.6 mmol, 1 eq) of $(Boc)_2O$ in 90 ml of anhydrous THF under the conditions described for the synthesis of 4, followed by purification by column chromatography (eluent petroleum ether/AcOEt 9:1), produced 10.5 g of the expected product in the form of white crystals following crystallization of the resulting light yellow oil in pentane (yield: 100%).

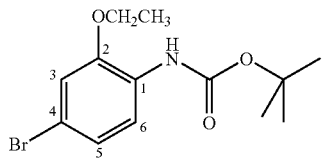

$C_{13}H_{18}BrNO_3$ M=316.98 g/mol F=72° C. $^1H$ NMR (CDCl$_3$) δ (ppm): 7.96 (d, J=8.6 Hz, 1H, $CH_{(6)}$); 7.03 (dd, J=8.6 Hz, J=2 Hz, 1H, $CH_{(5)}$); 6.98 (sl, 1H, NH); 6.92 (d, J=2 Hz, 1H, $CH_{(3)}$); 4.06 (q, J=7 Hz, 2H, $CH_2O$); 1.52 (s, 9H, $CH_3$); 1.45 (t, J=7 Hz, $CH_3$). $^{13}C$ NMR (CDCl$_3$) δ (ppm): 152.5 (CO$_2$); 147.4 (C$_2$); 127.4 (C$_1$); 123.7 (C$_5$); 119.1 (C$_6$); 114.4 (C$_4$); 113.3 (C$_3$); 80.6 ($\underline{C}$(CH$_3$)$_3$); 64.5 ($\underline{C}H_2O$); 28.3 (3C, $\underline{C}H_3$); 14.7 ($\underline{C}H_3$).

EXAMPLE 6 tert-butyl-N-{4-[allyl(dimethyl)silyl]-2-ethoxyphenyl}carbamate 7

The reaction between 5.3 g (16.8 mmol) of tert-butyl-N-(4-bromo-2-ethoxyphenyl)carbamate 5, 2.4 g (20.16 mmol, 1.2 eq) of 35% potassium hydride, 20.2 ml (34.4 mmol, 2.05 eq) of 1.5 M tert-butyllithium in hexane and 6 ml (40.3 mmol, 2.4 eq) of allyl(chloro)dimethylsilane according to the procedure described for compound 6, followed by two successive purifications by column chromatography (eluant petroleum ether/AcOEt 9:1), lead to 3.3 g of a colorless oil (yield: 58%).

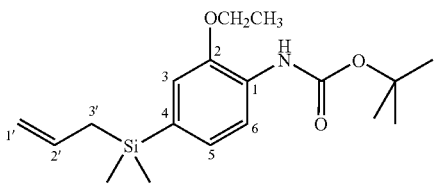

$C_{17}H_{27}NO_3Si$ M=335.56 g/mol $^1H$ NMR (CDCl$_3$) δ (ppm): 8.02 (d, J=8 Hz, 1H, $CH_{(6)}$); 7.10 (sl, 1H, NH); 7.06 (d, J=8 Hz, 1H, $CH_{(5)}$); 6.93 (s, 1H, $CH_{(3)}$); 5.78 (ddt, J=16.6 Hz, J=10.2 Hz, J=8.1 Hz, 1 H, $CH_{(2')}$); 4.89–4.83 (m, 2H, $CH_{2(1')}$); 4.12 (q, J=7 Hz, 3H, $CH_2O$); 1.74 (d, J=8.1 Hz, 2H, $CH_{2(3')}$); 1.54 (s, 9H, $CH_3$); 1.46 (t, J=7 Hz, 3H, $CH_3$); 0.25 (s, 6H, (CH$_3$)$_2$Si). $^{13}C$ NMR (CDCl$_3$) δ (ppm): 152.6 (CO$_2$); 146.2 (C$_2$); 134.8 (C$_{2'}$); 131.5 (C$_4$); 129 (C$_1$); 127 (C$_5$); 118 (C$_6$); 115.5 (C$_3$); 113 (C$_{1'}$); 80 ($\underline{C}$(CH$_3$)$_3$); 65 ($\underline{C}H_2O$); 28.5 (3C, $\underline{C}H_3$); 24 (C$_{3'}$); 15 ($\underline{C}H_3$); −3.4 (2C, $\underline{C}H_3Si$).

EXAMPLE 7 tert-butyl-N-(2-methoxyphenyl)carbamate Bonded to a Solid Support 8

In a 500 ml three-necked flask under an argon atmosphere, dissolve 6 g (18.7 mmol, 1.7 eq) of tert-butyl-N-{4-[allyl(dimethyl)silyl]-2-methoxyphenyl}carbamate 6 in 84 ml of anhydrous THF. Next, add 33.6 ml (16.8 mmol, 1.5 eq) of 0.5 M 9-BBN in anhydrous THF. The reaction is allowed to progress at room temperature and under argon for 5 hours. Then 0.4 g (0.33 mmol, 3% eq) of Pd(PPh$_3$)$_4$, 9 ml (1.7 eq) of an aqueous 2 M Na$_2$CO$_3$ solution, and 2.8 g (11 mmol) of bromopolystyrene resin (substituted 4 mmol/g) are added. The flask is wrapped in a sheet of aluminium foil and the THF is heated under a reflux condenser. After 40 hours, 0.4 g (0.33 mmol, 3% eq) of Pd(PPh$_3$)$_4$ catalyst is added and the reaction of THF under a reflux condenser for 24 hours is continued. The mixture is cooled to room temperature, then allowed to settle before filtering the resin on a Buchner funnel. The resin is washed successively with THF (4×30 ml), a 1% solution of diethyldithiocarbamic acid sodium salt in DMF (4×30 ml), a 1:1 mixture of THF/H$_2$O (4×30 ml), then H$_2$O (2×30 ml), MeOH (2×30 ml), DMF (2×30 ml), MeOH (2×30 ml), 3×[3×30 ml CH$_2$Cl$_2$, 3×30 ml MeOH] and, lastly, dried under vacuum (dessicator). 5.2 g of a light orange powder (yield: 70%) is obtained.

IR (KBr, cm$^{-1}$): 1730 (CO)

| | Elemental analysis: | |
|---|---|---|
| | Calc. | Exp. |
| % N | 2.8 | 1.95 |

EXAMPLE 8 tert-butyl-N-(2-ethoxyphenyl)carbamate Bonded on Solid Support 9

In a 500 ml three-necked flask under an argon atmosphere, 8 g (23.8 mmol, 1.7 eq) of tert-butyl-N-{4-[allyl(dimethyl)silyl]-2-ethoxyphenyl}carbamate 7 is mixed with 100 ml of anhydrous THF. Then 42.8 ml (21.4 mmol, 1.5 eq) of 0.5 M 9-BBN is added in anhydrous THF. The reaction is allowed to progress at room temperature and under argon for 4 hours. Then 0.5 g (0.42 mmol, 3% eq) of Pd(PPh$_3$)$_4$, 12 ml (1.7 eq) of an aqueous 2 M Na$_2$CO$_3$ solution, and 3.5 g (14 mmol) of bromopolystyrene resin (substituted 4 mmol/g) is added. The flask is wrapped in a sheet of aluminium foil and the THF is heated under a reflux condenser. After 40 hours, 0.5 g (0.42 mmol, 3% eq) of Pd(PPh$_3$)$_4$ catalyst is added and the reaction of THF under a reflux condenser for 24 hours is continued. The mixture is cooled to room temperature, then allowed to settle before filtering the resin on a Buchner funnel. The resin is washed successively with THF (4×40 ml), a 1% solution of diethyldithiocarbamic acid sodium salt in DMF (4×40 ml), a 1:1 mixture of THF/H$_2$O (4×40 ml), then H$_2$O (2×40 ml), MeOH (2×40 ml), DMF (2×40 ml), MeOH (2×40 ml), 3×[3×40 ml CH$_2$Cl$_2$, 3×40 ml MeOH] and, lastly, dried under vacuum (dessicator). 5.86 g of a light orange powder (yield: 80%) is obtained.

IR (cm$^{-1}$): 1729 (CO)

| | Elemental analysis: | |
|---|---|---|
| | Calc. | Exp. |
| % N | 2.76 | 2.23 |

EXAMPLE 9

2-methoxyaniline Bonded on Solid Support 10

1 g (2 mmol) of tert-butyl-N-(2-methoxyphenyl)carbamate (~2 mmol/g) bonded on solid support 8 is reacted with 1.2 g (8 mmol, 4 eq) of a 0.2 M solution of B-chlorocatecholborane in anhydrous $CH_2Cl_2$, the mixture is shaken at room temperature and under argon for 10 min. Next, 16 ml of water is added and shaken for an additional 20 min. Then the resin is filtered on a scintered filter and rinsed successively with 10% NaOH (60 ml), $H_2O$, DMF, MeOH, $CH_2Cl_2$, MeOH. After drying the resin in a dessicator, 0.8 g of a brown powder is obtained (yield: 98%).

IR (KBr, $cm^{-1}$): disappearance of the CO band at 1730 $cm^{-1}$

Elemental analysis:

|  | Calc. | Exp. |
|---|---|---|
| % N | 2.24 | 2.21 |

EXAMPLE 10

2-ethoxyaniline Bonded on Solid Support (11)

The reaction between 1.2 g (1.4 mmol) of tert-butyl-N-(2-ethoxyphenyl)carbamate (~1.2 mmol/g) bonded on solid support 9 and 0.87 g (5.66 mmol, 4 eq) of 0.2 M B-chlorocatecholborane in anhydrous $CH_2Cl_2$ according to the procedure described hereinabove, followed by filtration and washing, gave 1 g of a brown powder (yield: 95%).

IR ($cm^{-1}$): disappearance of the CO band at 1729 $cm^{-1}$

Elemental analysis:

|  | Calc. | Exp. |
|---|---|---|
| % N | 1.88 | 1.78 |

EXAMPLE 11

Cleavage of tert-butyl-N-(2-methoxyphenyl)carbamate Bonded on Solid Support (8)

0.35 g of tert-butyl-N-(2-methoxyphenyl)carbamate (theoretically 2 mmol/g) bonded on solid support 8 is reacted with 0.5 ml (7 mmol, 10 eq) of a 20% solution of $TFA/CH_2Cl_2$ at room temperature for 1 hour. The resin is filtered on a scintered filter and rinsed with $CH_2Cl_2$ and MeOH. Then, the filtrate is concentrated under vacuum, taken up in $CH_2Cl_2$, washed with a saturated aqueous $NaHCO_3$ solution. After drying on $MgSO_4$ and evaporation of the solvent, 31.1 mg of 2-methoxyaniline is obtained and characterized by the $^1H$ NMR spectrum and compared with the commercial product (yield: 36%). An IR control of the resin showed that the cleavage was not complete (presence of a carbonyl band at 1729 $cm^{-1}$). The resin was then reacted again with 10 equivalents of a 20% solution of $TFA/CH_2Cl_2$ for 15 hours at room temperature. After an identical treatment, 13.8 g of pure 2-methoxyaniline were obtained (overall yield: 52%).

EXAMPLE 12

2-bromoethyl-N-(2-methoxyphenyl)Carbamate (12)

In a 50 ml two-necked flask placed under an argon atmosphere, 1.5 g (7 mmol, 1.4 eq) of $(Boc)_2O$ is dissolved in 5 ml of anhydrous $CH_2Cl_2$. 61 mg (0.5 mol, 10% eq) of DMAP dissolved in 5 ml of anhydrous $CH_2Cl_2$ is added, then 0.56 ml (5 mmol) of 2-methoxyaniline is added dropwise. The mixture is stirred at room temperature for 20 min before adding 0.5 ml (7 mmol, 1.4 eq) of 2-bromoethanol diluted in 5 ml of anhydrous $CH_2Cl_2$. The reaction is allowed to progress for 30 min at room temperature then for approximately 20 hours under reflux of dichlormethane. Then, the medium is cooled and concentrated under vacuum. The resulting dark pink solid is purified by chromatography on a silica gel column (eluent $CH_2Cl_2$) to give 1.33 g of a colorless oil (yield: 95%).

$C_{10}H_{12}BrNO_3$ $M=274.12$ g/mol $^1H$ NMR ($CDCl_3$) δ (ppm): 8.05 (d, J=7.6 Hz, 1H, $CH_{(6)}$); 7.32 (sl, 1H, NH); 7.02–6.84 (m, 3H, $CH_{(3)}$, $CH_{(4)}$, $CH_{(5)}$); 4.47 (t, J=6 Hz, 2H, $CH_2O$); 3.86 (s, 3H, $OCH_3$); 3.57 (t, J=6 Hz, 2H, $CH_2Br$). $^{13}C$ NMR ($CDCl_3$) δ (ppm): 152.6 (CO); 147.6 ($C_2$); 127.2 ($C_1$); 123 ($C_4$); 121 ($C_6$); 118.2 ($C_5$); 110 ($C_3$); 64.4 ($\underline{C}H_2O$); 55.6 ($O\underline{C}H_3$); 29.1 ($\underline{C}H_2Br$).

GC (Rt, min, 70° C., 20° C./min): 6.92.

Elemental analysis:

|  | Calc. | Exp. |
|---|---|---|
| % C | 43.82 | 43.71 |
| % H | 4.41 | 4.52 |
| % N | 5.11 | 5.02 |

2-bromoethyl-N-(2-methoxyphenyl)carbamate (12)

The reaction between 0.15 g (~0.17 mmol) of 2-methoxyaniline resin 10 (~1.11 mmol/g), 0.25 g (1.2 mmol, 7 eq) of $(Boc)_2O$, 0.1 g (0.9 mmol, 5 eq) of DMAP, and 85 µl (1.2 mmol, 7 eq) of 2-bromoethanol in 6 to 8 ml of $CH_2Cl_2$ at room temperature for 16 hours according to the procedure described in example 12, followed by filtration and washing of the resin, yields an orange powder. Cleavage of the resin is carried out in 2 ml of TFA for 2 hours at room temperature. The resin is filtered and washed with $CH_2Cl_2$ and MeOH, and the filtrate is concentrated under vacuum. 27.3 mg of a brown oil (crude yield: 66%) is obtained. The composition of the crude mixture is analyzed by GC. The following products, among others, are obtained: 2-methoxyphenylaniline (15%), isocyanate intermediate (7%), 2–Chloroethyl-N-(2-methoxyphenyl)carbamate (5.2%) and 2-bromoethyl-N-(2-methoxyphenyl)carbamate 12 (59.4%).

GC/MS (Rt, min, 90° C., 30 s, 10° C./min, 220° C.; IE 70 eV): 5.62 (2-methoxyaniline, M=123), 6.07 (isocyanate, M=149), 14.00 (2–Chloroethyl-N-(2-methoxyphenyl)carbamate, M=229) and 15.24 (12.

EXAMPLE 13

Preparation of a Library of Carbamates Represented by Formula (I)

wherein $R_1$=OEt, Y=(CH2)m, mr=2 or 3, G=J=CH, n=1

An average mass of 90 mg of 2-ethoxyaniline resin 11 (~1.8 mmol/g) is weighed into 48 polypropylene reactors which are placed on the reaction block mounted on a Fisher Innova 2100 orbital shaker.

First Step: Formation of Carbamates Bonded to the Resin 4 ml of a solution prepared from 14.85 g (0.28 mol/l, 7 eq) of $(Boc)_2O$ and 5.94 g (0.20 mol/l, 5 eq) of DMAP dissolved in 240 ml of $CH_2Cl_2$ are distributed into each reactor. The reaction block is shaken for 30 min. To the first 24 reactors (matrix 1 to 24) 2 ml of a solution of 3.32 ml (0.56 mol/l, 7 eq) of 2-bromoethanol diluted in 70 ml of $CH_2Cl_2$ is addded and to the last 24 reactors (matrix 25 to 48) 2 ml of a solution of 3.55 ml (0.56 mmol/7 eq) of 3-bromopropanol diluted in 70 ml of $CH_2Cl_2$ is added. The reaction block is shaken at room temperature for 16 hours. The resins are filtered, then rinsed three times each with three successive solvents: DMF, MeOH, $CH_2Cl_2$ (4 ml/reactor per rinse). The resin is allowed to dry in air.

Second Step: N-alkylation Reaction 1.5 ml of a corresponding piperazine solution (1.6 mmol, 10 eq) previously prepared by dissolving the quantity to be weighed in 3.3 ml of $CH_2Cl_2$ is distributed into each reactor. A slight excess of each solution is prepared. The piperazines used and the amounts added in the reaction are listed below:

| Structure | MW | Quantity (g) |
|---|---|---|
| (phenyl-piperazine) | 162.24 | 0.578 |
| (2-OMe-phenyl-piperazine) | 192.26 | 0.685 |
| (3-OMe-phenyl-piperazine) | 192.26 | 0.685 |
| (4-OMe-phenyl-piperazine) | 192.26 | 0.685 |
| (2-Cl-phenyl-piperazine) | 196.68 | 0.700 |
| (3-Cl-phenyl-piperazine) | 196.68 | 0.700 |
| (4-Cl-phenyl-piperazine) | 196.68 | 0.700 |
| (2-CH3-phenyl-piperazine) | 176.26 | 0.628 |
| (3-CH3-phenyl-piperazine) | 176.26 | 0.628 |

-continued
| Structure | MW | Quantity (g) |
|---|---|---|
| 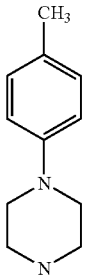 | 176.26 | 0.628 |
| 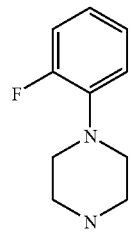 | 180.23 | 0.642 |
| 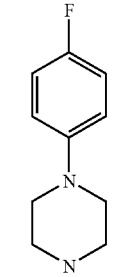 | 180.23 | 0.642 |
| 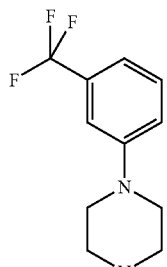 | 230.23 | 0.820 |
| 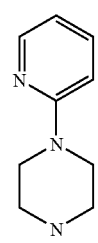 | 163.22 | 0.581 |
| 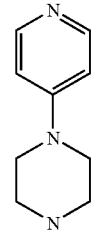 | 163.22 | 0.581 |
-continued
| Structure | MW | Quantity (g) |
|---|---|---|
| 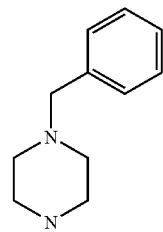 | 176.26 | 0.628 |
| 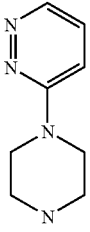 | 164.21 | 0.585 |
| 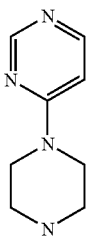 | 164.21 | 0.585 |
| 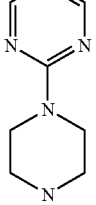 | 164.21 | 0.585 |
| 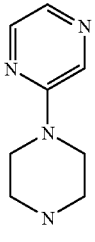 | 164.21 | 0.585 |
| 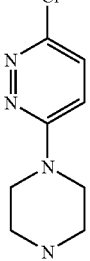 | 198.66 | 0.708 |

-continued

| Structure | MW | Quantity (g) |
|---|---|---|
| (2-chloropyrimidine-piperazine) | 198.66 | 0.708 |
| (2,5-dimethylphenyl-piperazine) | 190.29 | 0.678 |
| (3-methylpyridazine-piperazine) | 178.24 | 0.635 |

Next, 125 μl (4.5 eq) of DIEA to each reactor and shake the mixture at room temperature for 40 hours is added. The resins are filtered and rinsed three times each with three successive solvents: DMF, MeOH, $CH_2Cl_2$ (4 ml/reactor per rinse). The resin is allowed to dry in air.

Cleavage

Cleavage is carried out in 2 ml of TFA per reactor at room temperature for 2 hours. The resins are filtered and rinsed with 2×2 ml of $CH_2Cl_2$, and the filtrates are concentrated under vacuum.

Extraction in Alkaline Medium

The 48 mixtures are individually taken up in 8 ml of a 1:1 mixture of $CH_2Cl_2/H_2O$ in Whatman 12 ml cartridges equipped with a PTFE filter. The organic phase (=Organic phase A) is filtered, the aqueous phase is washed with 4 ml of $CH_2Cl_2$. The pH of the aqueous phase is adjusted to alkaline pH range by adding a saturated aqueous $Na_2CO_3$ solution. Then the aqueous phase is extracted with $CH_2Cl_2$ (1×4 ml then 1×2 ml). The 48 filtrates (=48 organic phase B) are vacuum concentrated.

Purification on Cation Exchange Resin

The cation exchange resin is a BCX resin packaged by Bodhan (Mettler-Toledo) in the form of 1 g SPE cartridges. The resin is first washed with 2×3 ml of MeOH (conditioning). The crude mixture, dissolved in 1 ml of MeOH and adjusted to pH 9 with a 1 M aqueous NaOH solution, is then deposited on the small resin column (loading). The column is then washed with 2×3 ml of MeOH (wash). The piperazine derivative is then released by elution with 3 ml of a 2 M solution of $NH_4OH$/MeOH (elution). The filtrate is concentrated under vacuum.

The resulting compounds represented by formula (I) are described and characterized as follows:

2-[4-(2-methoxyphenyl)piperazino]ethyl-N-(2-ethoxyphenyl)carbamate 14

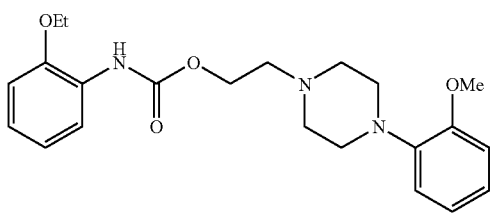

$C_{22}H_{29}N_3O_4$ M=399.49 g/mol Quantity: 2.2 mg (yield: 3%) HPLC: t=2.45 min MS: 400.68 ($MH^+$) HPLC purity: 85%

2-[4-(3-methoxyphenyl)piperazino]ethyl-N-(2-ethoxyphenyl)carbamate 15

Purification on a silica gel column (eluent AcOEt/petroleum ether 8:2 then AcOEt/petroleum ether/$NH_4OH$ 8:2:0.2) leads to the expected compound.

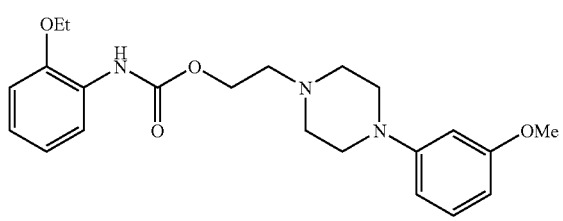

$C_{22}H_{29}N_3O_4$ M=399.49 g/mol Quantity: 6.8 mg (yield: 10%) HPLC: t=2.64 min MS: 400.51 ($MH^+$) HPLC purity: 94%

2-[4-(4-methoxyphenyl)piperazino]ethyl-N-(2-ethoxyphenyl)carbamate 16

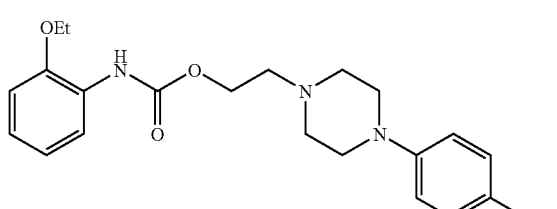

$C_{22}H_{29}N_3O_4$ M=399.49 g/mol Quantity: 3.4 mg (yield: 5%) HPLC: t=2.39 min MS: 400.68 ($MH^+$) HPLC purity: 86%

2-[4-(2–Chlorophenyl)piperazino]ethyl N-(2-ethoxyphenyl)carbamate 17

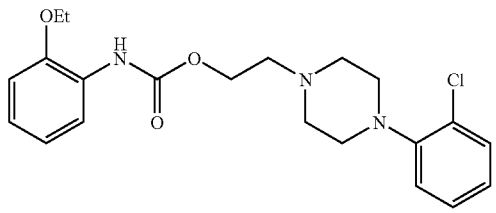

$C_{21}H_{26}ClN_3O_3$ M=403.91 g/mol Quantity: 1.7 mg (yield: 2%) HPLC: t=2.64 min MS: 404.63 (MH$^+$) HPLC purity: 77%

2-[4-(3–Chlorophenyl)piperazino]ethyl-N-(2-ethoxyphenyl)carbamate 18

Purification on a silica gel column (eluent AcOEt/petroleum ether 8:2 then AcOEt/petroleum ether/NH$_4$OH 8:2:0.2) leads to the expected compound.

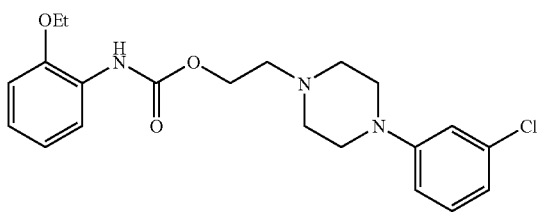

$C_{21}H_{26}ClN_3O_3$ M=403.91 g/mol Quantity: 8.5 mg (yield: 13%) HPLC: t=2.85 min MS: 404.46 (MH$^+$) HPLC purity: 96%

2-[4-(4–Chlorophenyl)piperazino]ethyl-N-(2-ethoxyphenyl)carbamate 19

Purification on a silica gel column (eluent AcOEt/petroleum ether 8:2 then AcOEt/petroleum ether/NH$_4$OH 8:2:0.2) ultimately leads to the expected compound.

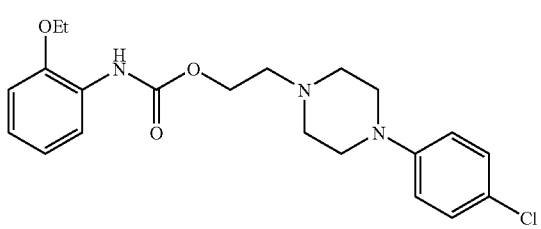

$C_{21}H_{26}ClN_3O_3$ M=403.91 g/mol Quantity: 7.3 mg (yield: 11%) HPLC: t=2.85 min MS: 404.47 (MH$^+$) HPLC purity: 85%

2-[4-(2-methylphenyl)pipeazino]ethyl-N-(2-ethoxyphenyl)carbamate 20

Purification on a silica gel column (eluent AcOEt/petroleum ether 8:2 then AcOEt/petroleum ether/NH$_4$OH 8:2:0.2) ultimately leads to the expected compound.

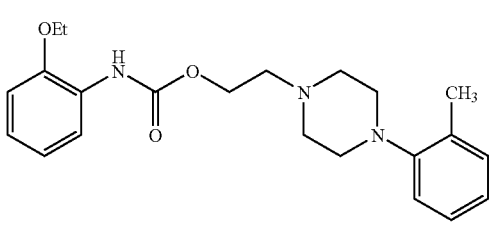

$C_{22}H_{29}N_3O_3$ M=383.49 g/mol Quantity: 7.1 mg (yield: 11%) HPLC: t=2.83 min MS: 384.51 (MH$^+$) HPLC purity: 74%

2-[4-(3-methylphenyl)piperazino]ethyl-N-(2-ethoxyphenyl)carbamate 21

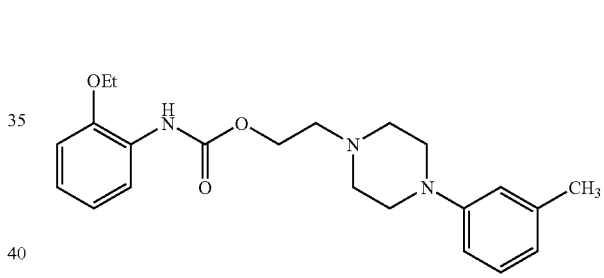

$C_{22}H_{29}N_3O_3$ CH$_3$ M=383.49 g/mol Quantity: 3.8 mg (yield: 6%) HPLC: t=2.73 min MS: 384.59 (MH$^+$) HPLC purity: 93%

2-[4-(4-methylphenyl)piperazino]ethyl-N-(2-ethoxyphenyl)carbamate 22

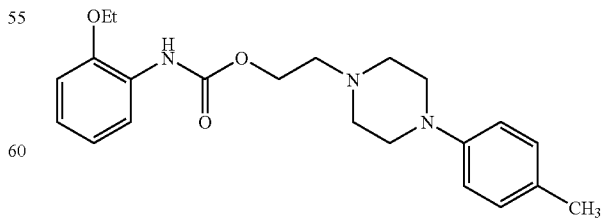

$C_{22}H_{29}N_3O_3$ M=383.49 g/mol Quantity: 3.2 mg (yield: 5%) HPLC: t=2.76 min MS: 384.60 (MH$^+$) HPLC purity: 56%

2-[4-(2-fluorophenyl)piperazino]ethyl-N-(2-ethoxyphenyl)carbamate 23

Purification on a silica gel column (eluent AcOEt/petroleum ether 8:2 then AcOEt/petroleum ether/NH$_4$OH 8:2:0.2) ultimately leads to the expected compound.

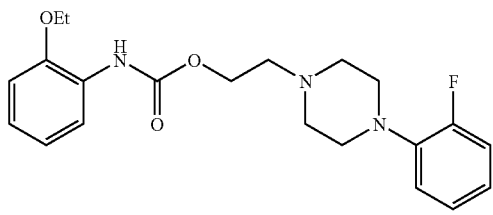

$C_{21}H_{26}FN_3O_3$ M=387.46 g/mol Quantity: 10.2 mg (yield: 16%) HPLC: t=2.63 min MS: 388.49 (MH$^+$) HPLC purity: 93%

2-[4-(2-pyridinyl)piperazino]ethyl-N-(2-ethoxyphenyl)carbamate 24

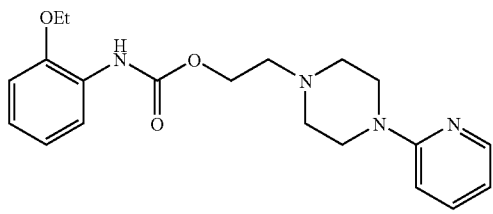

$C_{20}H_{26}N_4O_3$ M=370.46 g/mol Quantity: 7.6 mg (yield: 12%) HPLC: t=1.81 min MS: 371.56 (MH$^+$) HPLC purity: 55%

2-[4-(3-pyridazinyl)piperazino]ethyl-N-(2-ethoxyphenyl)carbamate 25

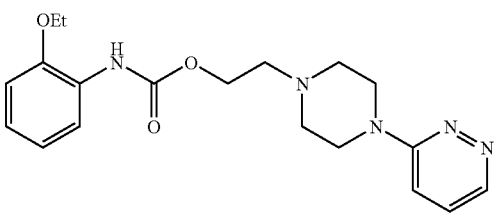

$C_{19}H_{25}N_5O_3$ M=371.44 g/mol Quantity: 4.3 mg (yield: 7%) HPLC: t=1.83 min MS: 372.55 (MH$^+$) HPLC purity: 27%

2-[4-(2-pyrimidinyl)piperazino]ethyl-N-(2-ethoxyphenyl)carbamate 26

Purification on a silica gel column (eluent AcOEt/petroleum ether 8:2 then AcOEt/petroleum ether/NH$_4$OH 8:2:0.2) leads to the expected compound.

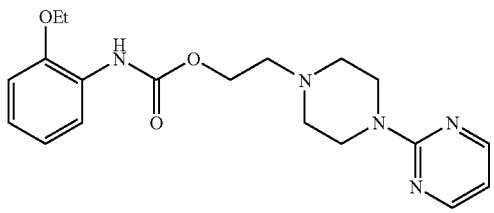

$C_{19}H_{25}N_5O_3$ M=371.44 g/mol Quantity: 10.1 mg (yield: 16%) HPLC: t=2.26 min MS: 372.49 (MH$^+$) HPLC purity: 94%

2-[4-(6-2chloro-3-pyridazinyl)piperazino]ethyl-N-(2-ethoxyphenyl)carbamate 27

Purification on a silica gel column (eluent AcOEt/petroleum ether 8:2 then AcOEt/petroleum ether/NH$_4$OH 8:2:0.2) leads to the expected compound.

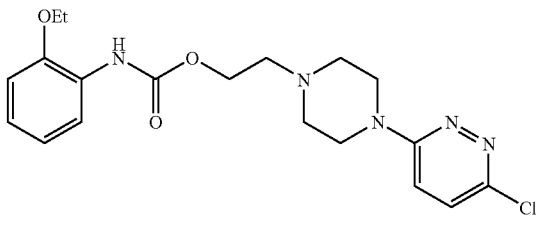

$C_{19}H_{24}ClN_5O_3$ M=405.89 g/mol Quantity: 6.8 mg (yield: 10%) HPLC: t=2.27 min MS: 406.47 (MH$^+$) HPLC purity: 89%

2-[4-(6-methyl-3-pyridazinyl)piperazino]ethyl-N-(2-ethoxyphenyl)carbamate 28

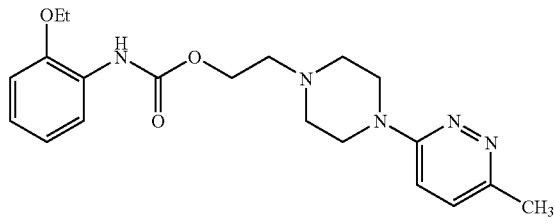

$C_{20}H_{27}N_5O_3$ M=385.47 g/mol Quantity: 7 mg (yield: 11%) HPLC: t=2.13 min MS: 386.58 (MH$^+$) HPLC purity: 61%

3-[4-(2-methoxyphenyl)piperazino]propyl-N-(2-ethoxyphenyl)carbamate 29

Purification on a silica gel column (eluent AcOEt/petroleum ether 8:2 then AcOEt/petroleum ether/NH$_4$OH 8:2:0.2) leads to the expected compound.

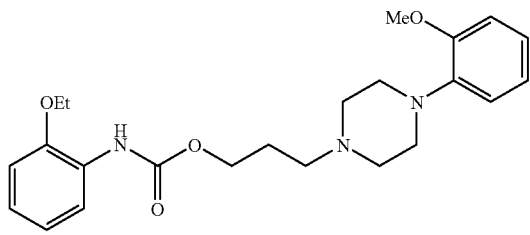

C$_{23}$H$_{31}$N$_3$O$_4$ M=413.52 g/mol Quantity: 14.7 mg (yield: 22%) HPLC: t=2.57 min MS: 414.55 (MH$^+$) HPLC purity: 100%

3-[4-(3-methoxyphenyl)piperazino]propyl-N-(2-ethoxyphenyl)carbamate 30

Purification on a silica gel column (eluent AcOEt/petroleum ether 8:2 then AcOEt/petroleum ether/NH$_4$OH 8:2:0.2) leads to the expected compound.

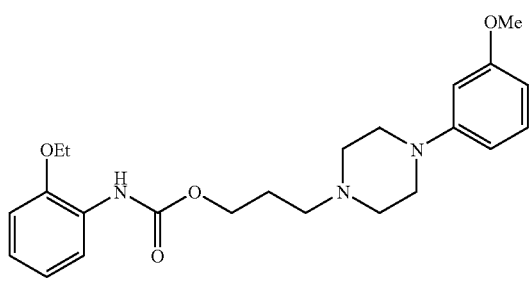

C$_{23}$H$_{31}$N$_3$O$_4$ M=413.52 g/mol Quantity: 11.5 mg (yield: 17%) HPLC: t=2.62 min MS: 414.55 (MH$^+$) HPLC purity: 98%

3-[4-(2–Chlorophenyl)piperazino]propyl-N-(2-ethoxyphenyl)carbamate 31

Purification on a silica gel column (eluent AcOEt/petroleum ether 8:2 then AcOEt/petroleum ether/NH$_4$OH 8:2:0.2) leads to the expected compound.

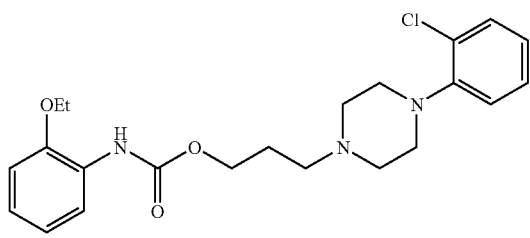

C$_{22}$H$_{28}$ClN$_3$O$_3$ M=417.94 g/mol Quantity: 14.1 mg (yield: 20%) HPLC: t=2.79 min MS: 418.50 (MH$^+$) HPLC purity: 94%

3-[4-(3–Chlorophenyl)piperazino]propyl-N-(2-ethoxyphenyl)carbamate 32

Purification on a silica gel column (eluent AcOEt/petroleum ether 8:2 then AcOEt/petroleum ether/NH$_4$OH 8:2:0.2) leads to the expected compound.

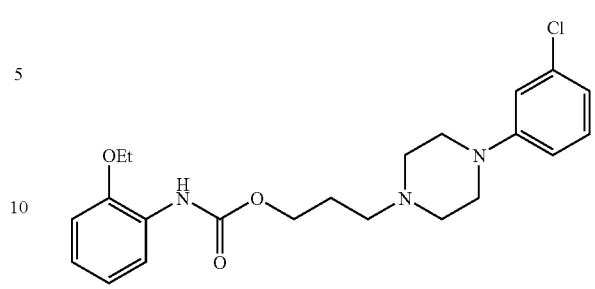

C$_{22}$H$_{28}$ClN$_3$O$_3$ M=417.94 g/mol Quantity: 13.3 mg (yield: 19%) HPLC: t=2.83 min MS: 418.51 (MH$^+$) HPLC purity: 100%

3-[4-(4–Chlorophenyl)piperazino]propyl-N-(2-ethoxyphenyl)carbamate 33

Purification on a silica gel column (eluent AcOEt/petroleum ether 8:2 then AcOEt/petroleum ether/NH$_4$OH 8:2:0.2) leads to the expected compound.

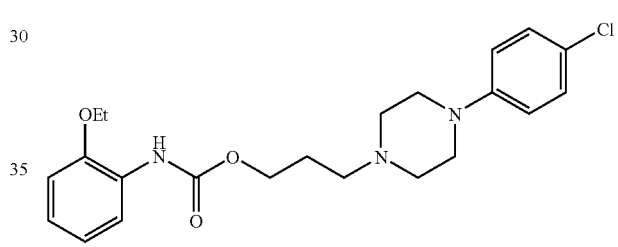

C$_{22}$H$_{28}$ClN$_3$O$_3$ M=417.94 g/mol Quantity: 0 mg (yield: 14%) HPLC: t=2.87 min MS: 418.50 (MH$^+$) HPLC purity: 94%

3-[4-(2-methylphenyl)piperazino]propyl N-(2-ethoxyphenyl)carbamate 34

Purification on a silica gel column (eluent AcOEt/petroleum ether 8:2 then AcOEt/petroleum ether/NH$_4$OH 8:2:0.2) leads to the expected compound.

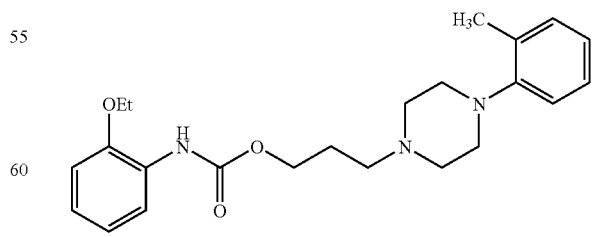

C$_{23}$H$_{31}$N$_3$O$_3$ M=397.52 g/mol Quantity: 7.2 mg (yield: 11%) HPLC: t=2.87 min MS: 398.55 (MH$^+$) HPLC purity: 100%-

3-[4-(3-methylphenyl)piperazino]propyl-N-(2-ethoxyphenyl)carbamate 35

Purification on a silica gel column (eluent AcOEt/petroleum ether 8:2 then AcOEt/petroleum ether/NH$_4$OH 8:2:0.2) leads to the expected compound.

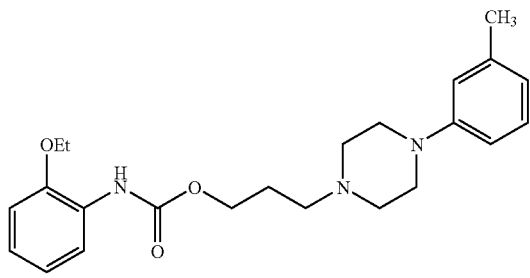

$C_{23}H_3N_3O_3$ M=397.52 g/mol Quantity: 10.7 mg (yield: 16%) HPLC: t=2.80 min MS: 398.55 (MH$^+$) HPLC purity: 95%

3-[4-(4-methylphenyl)piperazino]propyl-N-(2-ethoxyphenyl)carbamate 36

Purification on a silica gel column (eluent AcOEt/petroleum ether 8:2 then AcOEt/petroleum ether/NH$_4$OH 8:2:0.2) leads to the expected compound.

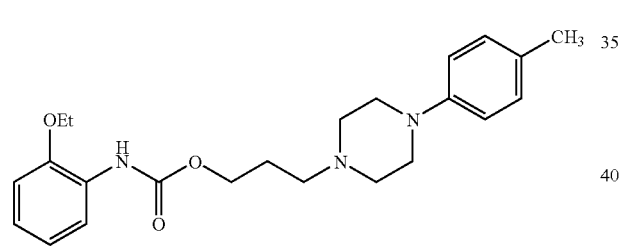

$C_{23}H_{31}N_3O_3$ M=397.52 g/mol Quantity: 8.7 mg (yield: 13%) HPLC: t=2.77 min MS: 398.56 (MH$^+$) HPLC purity: 90%

3-[4-(2-fluorophenyl)piperazino]propyl-N-(2-ethoxyphenyl)carbamate 37

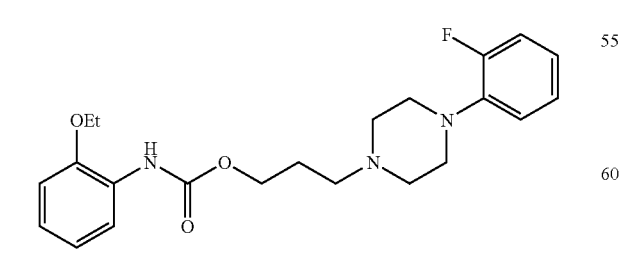

$C_{22}H_{28}FN_3O_3$ M=401.49 g/mol Quantity: 1 mg (yield: 1%) HPLC: t=2.71 min MS: 402.57 (MH$^+$) HPLC purity: 44%

3-[4-(4-fluorophenyl)piperazino]propyl-N-(2-ethoxyphenyl)carbamate 38

Purification on a silica gel column (eluent AcOEt/petroleum ether 8:2 then AcOEt/petroleum ether/NH$_4$OH 8:2:0.2) leads to the expected compound.

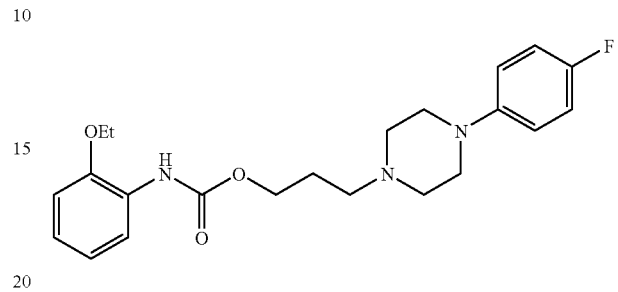

$C_{22}H_{28}FN_3O_3$ M=401.49 g/mol Quantity: 11.9 mg (yield: 18%) HPLC: t=2.66 min MS: 402.53 (MH$^+$) HPLC purity: 82%

3-{4-[3-(trifluoromethyl)phenyl]piperazino}propyl-N-(2-ethoxyphenyl)carbamate 39

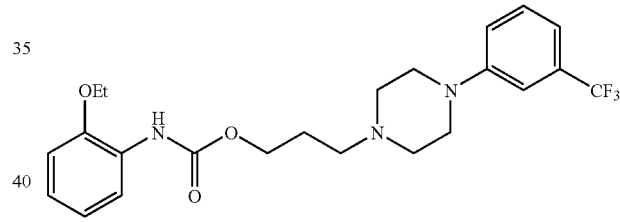

$C_{23}H_{28}F_3N_3O_3$ M=451.49 g/mol Quantity: 50.5 mg (yield: 69%) HPLC: t=2.87 min MS: 452.52 (MH$^+$) HPLC purity: 85%

3-[4-(2-pyridinyl)piperazino]propyl-N-(2-ethoxyphenyl)carbamate 40

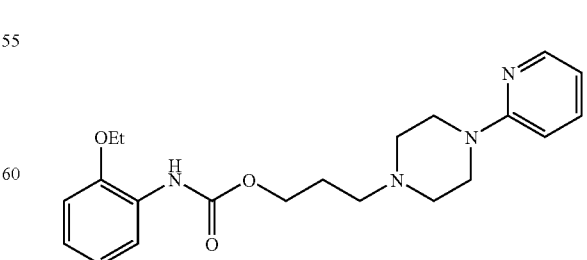

$C_{21}H_{28}N_4O_3$ M=384.48 g/mol Quantity: 6 mg (yield: 9%) HPLC: t=1.98 min MS: 385.56 (MH$^+$) HPLC purity: 100%

3-[4-(4-pyridinyl)piperazino]propyl-N-(2-ethoxyphenyl)carbamate 41

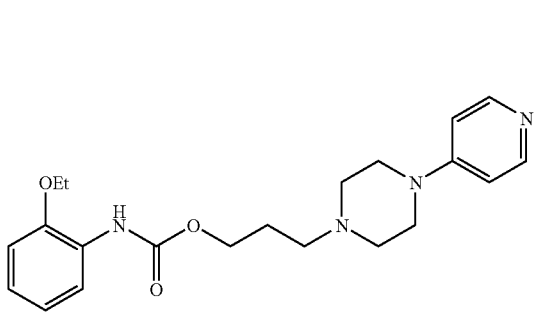

$C_{21}H_{28}N_4O_3$ M=384.48 g/mol Quantity: 8.7 mg (yield: 14%) HPLC: t=1.90 min MS: 385.56 (MH$^+$) HPLC purity: 100%

3-[4-(3-pyridazinyl)piperazino]propyl-N-(2-ethoxyphenyl)carbamate 42

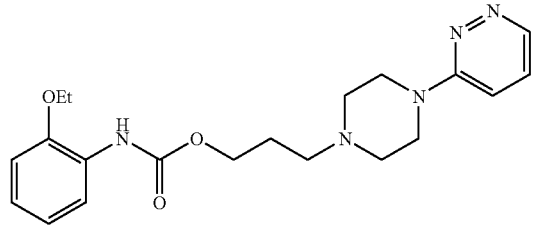

$C_{20}H_{27}N_5O_3$ M=385.47 g/mol Quantity: 6.1 mg (yield: 9%) HPLC: t=1.94 min MS: 386.56 (MH$^+$) HPLC purity: 96%

3-[4-(4-pyrimidinyl)piperazino]propyl-N-(2-ethoxyphenyl)carbamate 43

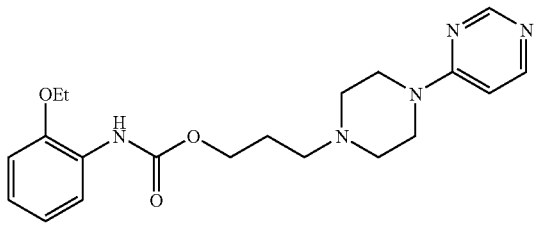

$C_{20}H_{27}N_5O_3$ M=385.47 g/mol Quantity: 8.5 mg (yield: 13%) HPLC: t=1.86 min MS: 386.55 (MH$^+$) HPLC purity: 100%

3-[4-(2-pyrimidinyl)piperazino]propyl-N-(2-ethoxyphenyl)carbamate 44

Purification on a silica gel column (eluent AcOEt/petroleum ether 8:2 then AcOEt/petroleum ether/NH$_4$OH 8:2:0.2) leads to the expected compound.

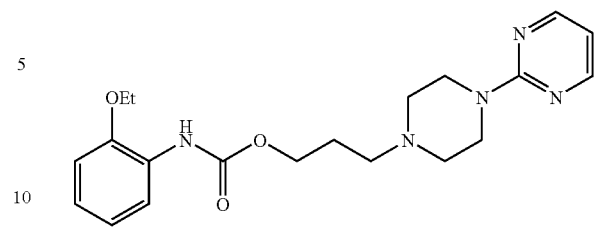

$C_{20}H_{27}N_5O_3$ M=385.47 g/mol Quantity: 16.9 mg (yield: 27%) HPLC: t=2.27 min MS: 386.52 (MH$^+$) HPLC purity: 97%

3-[4-(2-pyrazinyl)piperazino]propyl-N-(2-ethoxyphenyl)carbamate 45

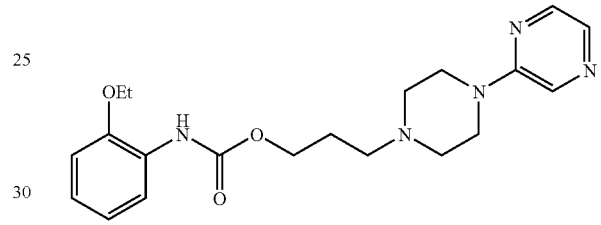

$C_{20}H_{27}N_5O_3$ M=385.47 g/mol Quantity: 2.3 mg (yield: 3%) HPLC: t=2.19 min MS: 386.55 (MH$^+$) HPLC purity: 79%

3-[4-(6–Chloro-3-pyridazinyl)piperazino]propyl-N-(2-ethoxyphenyl)carbamate 46

Purification on a silica gel column (eluent AcOEt/petroleum ether 8:2 then AcOEt/petroleum ether/NH$_4$OH 8:2:0.2) leads to the expected compound.

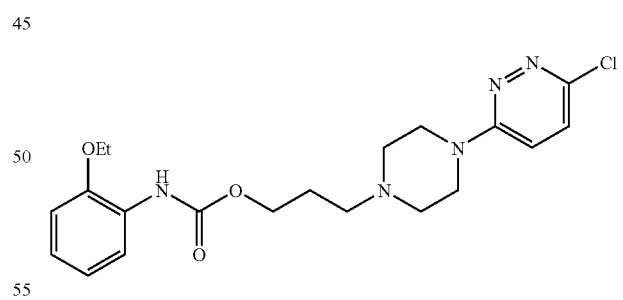

$C_{20}H_{26}ClN_5O_3$ M=419.91 g/mol Quantity: 10.7 mg (yield: 15%) HPLC: t=2.32 min MS: 420.50 (MH$^+$) HPLC purity: 100%

3-[4-(2,5-dimethylphenyl)piperazino]propyl-N-(2-ethoxyphenyl)carbamate 47

Purification on a silica gel column (eluent AcOEt/petroleum ether 8:2 then AcOEt/petroleum ether/NH$_4$OH 8:2:0.2) leads to the expected compound.

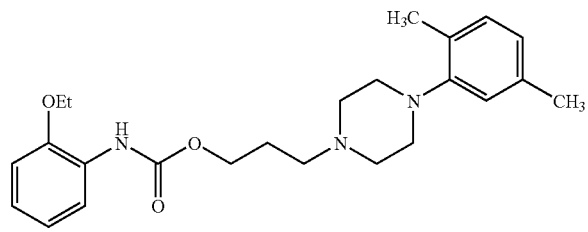

C₂₄H₃₃N₃O₃ M=411.55 g/mol Quantity: 7.5 mg (yield: 11%) HPLC: t=3.02 min MS: 412.58 (MH⁺) HPLC purity: 85%

3-[4-(6-methyl-3-pyridazinyl)piperazino]propyl-N-(2-ethoxyphenyl)carbamate 48

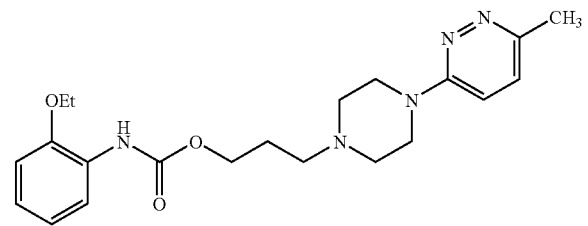

C₂₁H₂₉N₅O₃ M=399.50 g/mol Quantity: 7.7 mg (yield: 11%) HPLC: t=1.88 min MS: 400.58 (MH⁺) HPLC purity: 100%

EXAMPLE 14

Preparation of a Library of Carbamates Represented by Formula (I)

wherein

R₁=OMe, Y=(CH2)*m*, m=2 or 3, G=J=CH, n=1

An average mass of 90 mg of 2-methoxyaniline resin 10 (~1.3 mmol/g) is weighed into 44 polypropylene reactors which are placed on the reaction block mounted on the orbital shaker.

First Step: Formation of Carbamates 4 ml of a solution prepared from 9.82 g (0.20 mol/l, 7 eq) of (Boc)₂O and 3.93 g (0.14 mol/l, 5 eq) of DMAP dissolved in 220 ml of CH₂Cl₂ are distributed into each reactor. The reaction block is shaken for 30 min. To the first 22 reactors 2 ml of a solution of 4.8 ml (82 mmol/l, 14 eq) of 2-bromoethanol diluted in 70 ml of CH₂Cl₂ is added, and to the last 22 reactors 2 ml of a solution of 5.2 ml (82 mmol/l, 14 eq) of 3-bromopropanol diluted in 70 ml of CH₂Cl₂ is added. The reaction block is shaken at room temperature for 28 hours. The shaker is stopped. The resins are filtered then rinsed three times each with three successive solvents: DMF, MeOH, CH₂Cl₂ (4 ml/reactor per rinse). The resin is allowed to dry in air.

Second Step: N-Alkylation Reaction 1.2 ml of a corresponding piperazine solution (1.2 mmol, 10 eq) previously prepared is distributed into each reactor. The piperazines used and the amounts added to the reaction are listed below:

| Structure | MW | Quantity (g) |
|---|---|---|
| (phenyl-piperazine) | 162.24 | 0.417 |
| (2-OMe-phenyl-piperazine) | 192.26 | 0.494 |
| (3-OMe-phenyl-piperazine) | 192.26 | 0.494 |
| (4-OMe-pyridyl-piperazine) | 192.26 | 0.494 |
| (2-Cl-phenyl-piperazine) | 196.68 | 0.506 |
| (3-Cl-phenyl-piperazine) | 196.68 | 0.506 |

-continued
| Structure | MW | Quantity (g) |
|---|---|---|
| 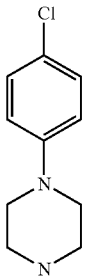 | 196.68 | 0.506 |
| 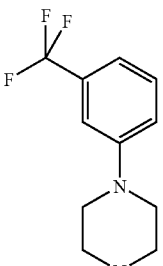 | 176.26 | 0.453 |
| 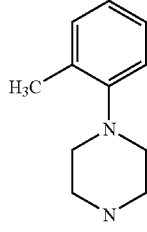 | 176.26 | 0.453 |
| 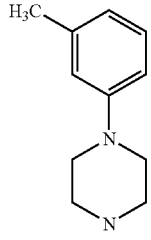 | 176.26 | 0.453 |
| 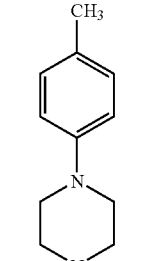 | 180.23 | 0.463 |
| 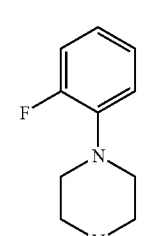 | 180.23 | 0.463 |
-continued
| Structure | MW | Quantity (g) |
|---|---|---|
| 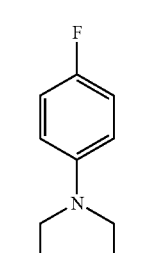 | 230.23 | 0.592 |
| 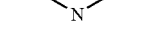 | 163.22 | 0.420 |
| 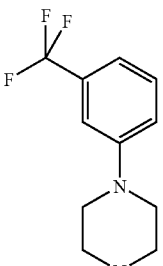 | 163.22 | 0.420 |
| 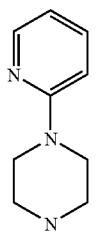 | 176.26 | 0.453 |
| 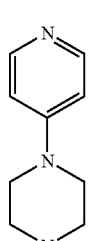 | 164.21 | 0.422 |
| 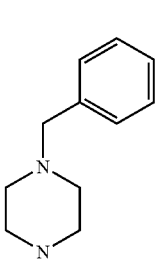 | 164.21 | 0.422 |

35

-continued

| Structure | MW | Quantity (g) |
|---|---|---|
| (pyrazine-piperazine) | 164.21 | 0.422 |
| (6-chloropyridazine-piperazine) | 198.66 | 0.511 |
| (2-chloropyrimidine-piperazine) | 198.66 | 0.511 |
| (2,5-dimethylphenyl-piperazine) | 190.29 | 0.489 |

Next, 75 µl (3.5 eq) of DIEA is added to each well and shaken at room temperature for 40 hours. The resins are filtered and rinsed three times each with three successive solvents: DMF, MeOH, CH₂Cl₂ (4 ml/reactor per rinse). The resin is allowed to dry in air.

Cleavage

Cleavage is carried out in 2 ml of TFA per reactor at room temperature for 2 hours. The resins are filtered and rinsed with 2×2 ml of CH₂Cl₂, then the filtrates are concentrated. Each filtrate is taken up in 1 ml of MeOH, the pH is adjusted to 9 with an aqueous 1 M NaOH solution. The mixtures are then purified on cation exchange resins according to the protocol described hereinabove. The 44 filtrates collected into previously tared tubes are vacuum concentrated (Genevac) and analyzed by HPLC/MS before being weighed.

36

2-(4-phenylpiperazino)ethyl-N-(2-methoxyphenyl) carbamate 49

$C_{20}H_{25}N_3O_3$ M=355.44 g/mol Quantity: 4.4 mg (yield: 10%) HPLC: t=2.41 min MS: 356.46 (MH$^+$) HPLC purity: 85%

2-[4-(2-methoxyphenyl)piperazino]ethyl-N-(2-methoxyphenyl)carbamate 50

$C_{21}H_{27}N_3O_4$ M=385.47 g/mol Quantity: 3.5 mg (yield: 7%) HPLC: t=2.44 min MS: 386.49 (MH$^+$) HPLC purity: 99%

2-[4-(3-methoxyphenyl)piperazino]ethyl-N-(2-methoxyphenyl)carbamate 51

$C_{21}H_{27}N_3O_4$ M=385.47 g/mol Quantity: 2.8 mg (yield: 6%) HPLC: 2.46 min MS: 386.49 (MH$^+$) HPLC purity: 92%

2-[4-(4-methoxyphenyl)piperazino]ethyl-N-(2-methoxyphenyl)carbamate 52

$C_{21}H_{27}N_3O_4$ M=385.47 g/mol Quantity: 7.9 mg (yield: 17%) HPLC: t=2.39 min MS: 386.49 (MH$^+$) HPLC purity: 88%

2-[4-(2–Chlorophenyl)piperazino]ethyl-N-(2-methoxyphenyl)carbamate 53

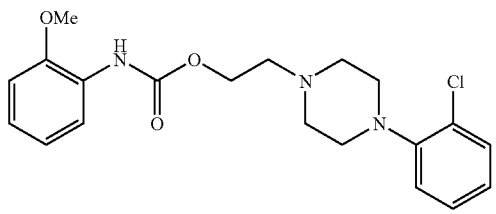

$C_{20}H_{24}ClN_3O_3$ M=389.89 g/mol Quantity: 5.6 mg (yield: 12%) HPLC: t=2.62 min MS: 390.44 (MH$^+$) HPLC purity: 97%

2-[4-(3–Chlorophenyl)piperazino]ethyl-N-(2-methoxyphenyl)carbamate 54

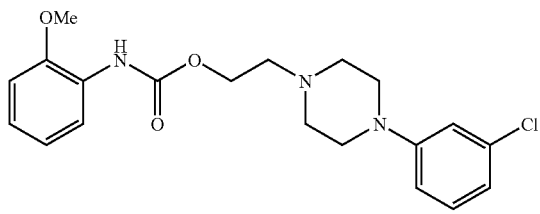

$C_{20}H_{24}ClN_3O_3$ M=389.89 g/mol Quantity: 3.1 mg (yield: 6%) HPLC: t=2.70 min MS: 390.44 (MH$^+$) HPLC purity: 91%

2-[4-(4–Chlorophenyl)piperazino]ethyl-N-(2-methoxyphenyl)carbamate 55

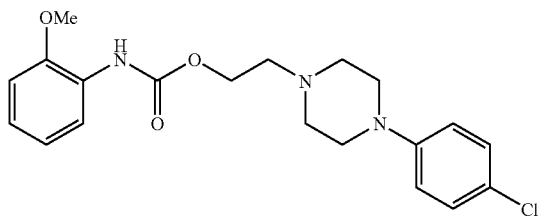

$C_{20}H_{24}ClN_3O_3$ M=389.89 g/mol Quantity: 6.4 mg (yield: 14%) HPLC: 2.69 min MS: 390.44 (MH$^+$) HPLC purity: 78%

2-[4-(2-methylphenyl)piperazino]ethyl-N-(2-methoxyphenyl)carbamate 56

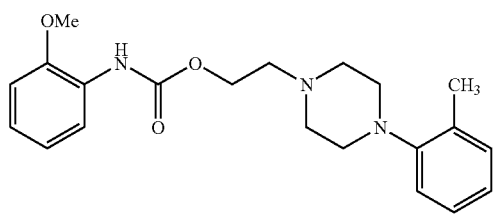

$C_{21}H_{27}N_3O_3$ M=369.47 g/mol Quantity: 8.4 mg (yield: 19%) HPLC: t=2.61 min MS: 370.49 (MH$^+$) HPLC purity: 84%

2-[4-(3-methylphenyl)piperazino]ethyl-N-(2-methoxyphenyl)carbamate 57

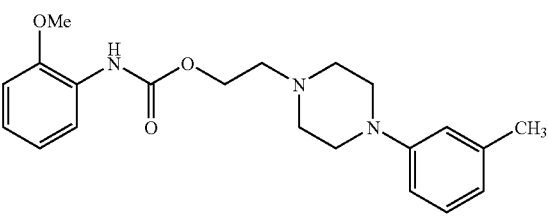

$C_{21}H_{27}N_3O_3$ M=369.47 g/mol Quantity: 4.1 mg (yield: 9%) HPLC: t=2.59 min MS: 370.50 (MH$^+$) HPLC purity: 93%

2-[4-(4-methylphenyl)piperazino]ethyl-N-(2-methoxyphenyl)carbamate 58

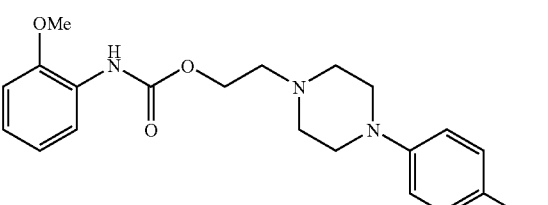

$C_{21}H_{27}N_3O_3$ M=369.47 g/mol Quantity: 4.8 mg (yield: 11%) HPLC: t=2.61 min MS: 370.50 (MH$^+$) HPLC purity: 88%

2-[4-(2-fluorophenyl)piperazino]ethyl-N-(2-methoxyphenyl)carbamate 59

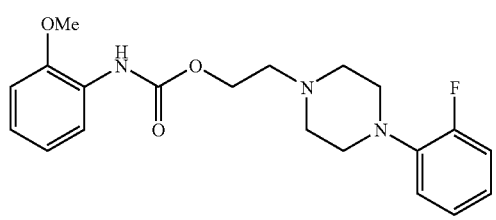

$C_{20}H_{24}FN_3O_3$ M=373.43 g/mol Quantity: 4.8 mg (yield: 11%) HPLC: t=2.50 min MS: 374.48 (MH$^+$) HPLC purity: 96%

2-[4-(4-fluorophenyl)piperazino]ethyl-N-(2-methoxyphenyl)carbamate 60

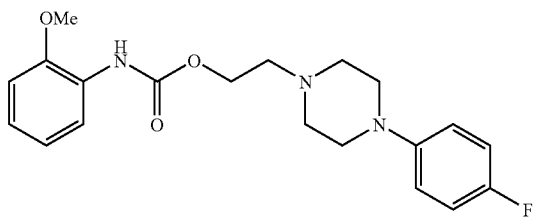

$C_{20}H_{24}FN_3O_3$ M=373.43 g/mol Quantity: 1.6 mg (yield: 3%) HPLC: t=2.52 min MS: 374.48 (MH$^+$) HPLC purity: 79%

2-{4-[3-(trifluoromethyl)phenyl]piperazino}ethyl-N-(2-methoxyphenyl)carbamate 61

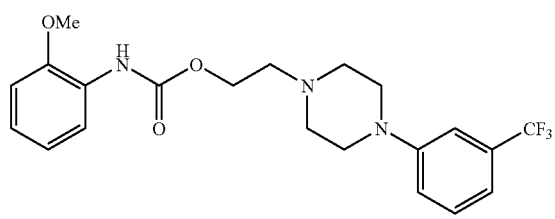

$C_{20}H_{24}F_3N_3O_3$ M=423.44 g/mol Quantity: 4.2 mg (yield: 8%) HPLC: t=2.83 min MS: 424.50 (MH$^+$) HPLC purity: 91%

2-[4-(2-pyridinyl)piperazino]ethyl-N-(2-methoxyphenyl)carbamate 62

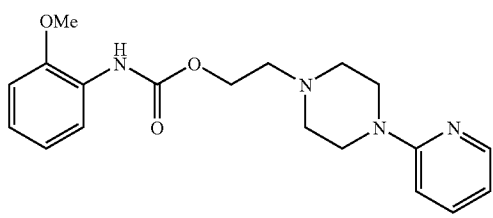

$C_{19}H_{24}N_4O_3$ M=356.43 g/mol Quantity: 5.3 mg (yield: 12%) HPLC: t=2.03 min MS: 357.48 (MH$^+$) HPLC purity: 80%

2-[4-(4-pyridinyl)piperazino]ethyl-N-(2-methoxyphenyl)carbamate 63

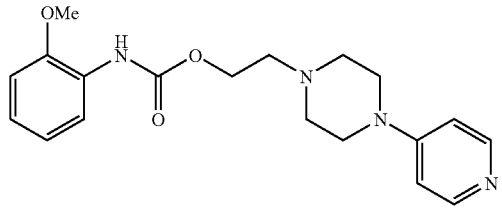

$C_{19}H_{24}N_4O_3$ M=356.43 g/mol Quantity: 1.8 mg (yield: 4%) HPLC: t=2.08 min MS: 357.48 (MH$^+$) HPLC purity: 83%

2-[4-(3-pyridazinyl)piperazino]ethyl-N-(2-methoxyphenyl)carbamate 64

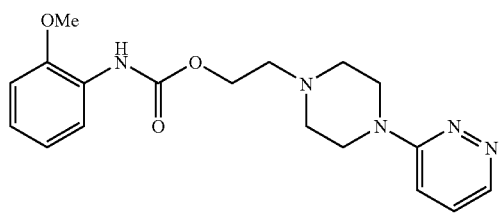

$C_{18}H_{23}N_5O_3$ M=357.42 g/mol Quantity: 2.9 mg (yield: 7%) HPLC: t=1.97 min MS: 358.48 (MH$^+$) HPLC purity: 87%

2-[4-(2-pyrimidinyl)piperazino]ethyl-N-(2-methoxyphenyl)carbamate 65

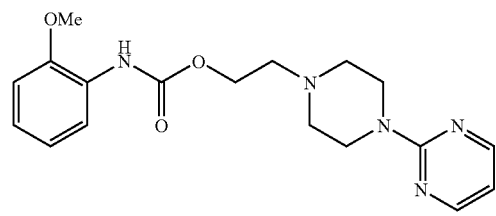

$C_{18}H_{23}N_5O_3$ M=357.42 g/mol Quantity: 4.3 mg (yield: 10%) HPLC: t=2.09 min MS: 358.48 (MH$^+$) HPLC purity: 99%

2-[4-(2-pyrazinyl)piperazino]ethyl-N-(2-methoxyphenyl)carbamate 66

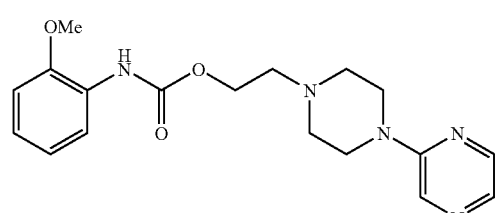

$C_{18}H_{23}N_5O_3$ M=357.42 g/mol Quantity: 4.5 mg (yield: 10%) HPLC: t=1.99 min MS: 358.48 (MH⁺) HPLC purity: 97%

2-{4-[3-(6–Chloro)pyridazinyl]piperazino}ethyl-N-(2-methoxyphenyl)carbamate 67

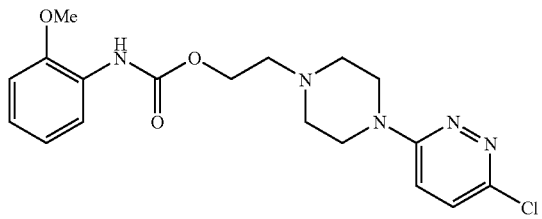

$C_{18}H_{22}ClN_5O_3$ M=391.86 g/mol Quantity: 5.1 mg (yield: 11%) HPLC: t=2.11 min MS: 392.46 (MH⁺) HPLC purity: 80%

2-[4-(2,5-dimethylphenyl)piperazino]ethyl-N-(2-methoxyphenyl)carbamate 68

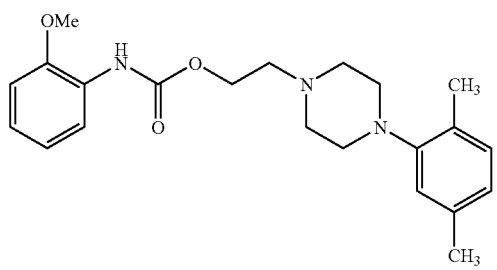

$C_{22}H_{29}N_3O_3$ M=383.49 g/mol Quantity: 4.8 mg (yield: 10%) HPLC: t=2.8 min MS: 384.54 (MH⁺) HPLC purity: 93%

3-(4-phenylpiperazino)propyl-N-(2-methoxyphenyl)carbamate 69

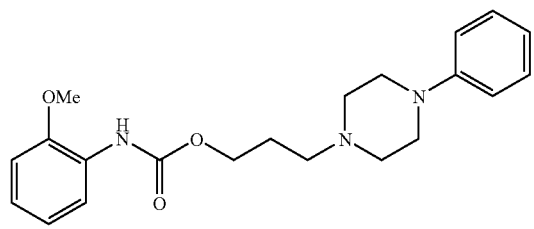

$C_{21}H_{27}N_3O_3$ M=369.47 g/mol Quantity: 14.1 mg (yield: 32%) HPLC: t=2.39 min MS: 370.52 (MH⁺) HPLC purity: 98%

3-[4-(2-methoxyphenyl)piperazino]propyl-N-(2-methoxyphenyl)carbamate 70

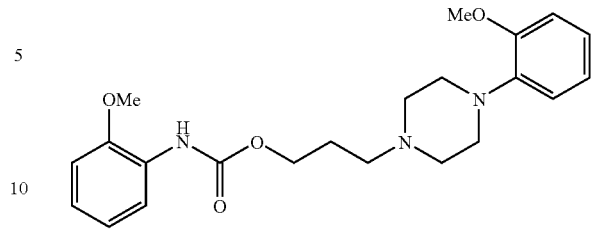

$C_{22}H_{29}N_3O_4$ M=369.47 g/mol Quantity: 15.3 mg (yield: 32%) HPLC: t=2.42 min MS: 370.52 (MH⁺) HPLC purity: 98%

3-[4-(3-methoxyphenyl)piperazino]propyl-N-(2-methoxyphenyl)carbamate 71

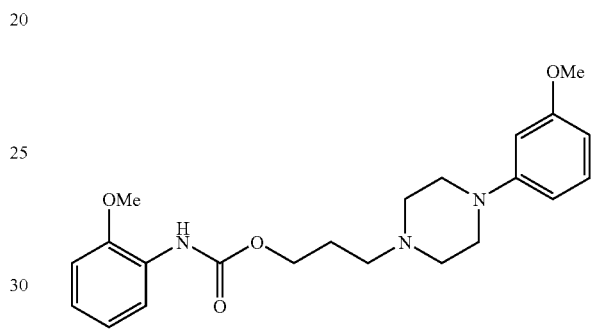

$C_{22}H_{29}N_3O_4$ M=369.47 g/mol Quantity: 8.9 mg (yield: 19%) HPLC: t=2.48 min MS: 370.52 (MH⁺) HPLC purity: 89%

3-[4-(4-methoxyphenyl)piperazino]propyl-N-(2-methoxyphenyl)carbamate 72

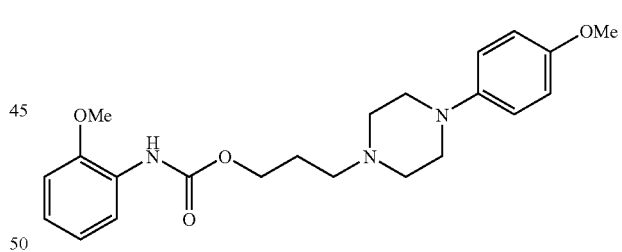

$C_{22}H_{29}N_3O_4$ M=369.47 g/mol Quantity: 15.2 mg (yield: 32%) HPLC: t=2.31 min MS: 370.52 (MH⁺) HPLC purity: 98%

3-[4-(2–Chlorophenyl)piperazino]propyl-N-(2-methoxyphenyl)carbamate 73

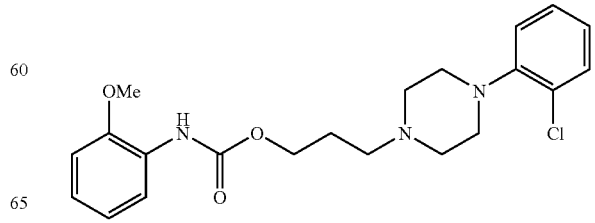

$C_{21}H_{26}ClN_3O_3$ M=403.91 g/mol Quantity: 14.5 mg (yield: 30%) HPLC: t=2.59 min MS: 404.51 (MH⁺) HPLC purity: 98%

3-[4-(3-Chlorophenyl)piperazino]propyl N-(2-methoxyphenyl)carbamate 74

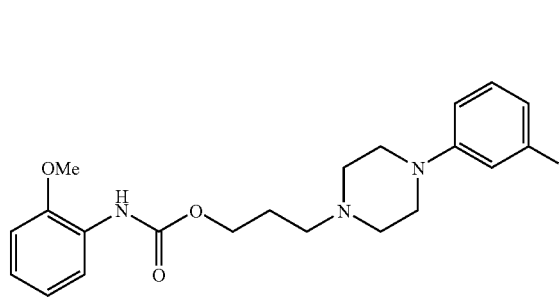

$C_{21}H_{26}ClN_3O_3$ M=403.91 g/mol Quantity: 13.1 mg (yield: 27%) HPLC: t=2.63 min MS: 404.50 (MH⁺) HPLC purity: 97%

3-[4-(4-Chlorophenyl)piperazino]propyl-N-(2-methoxyphenyl)carbamate 75

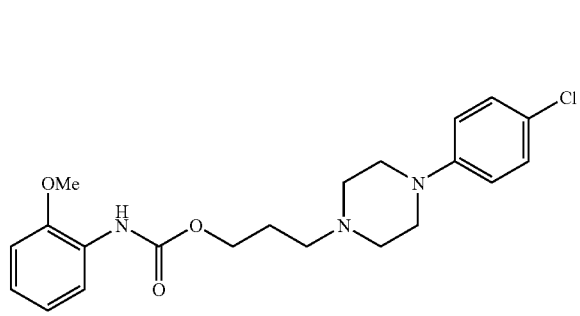

$C_{21}H_{26}ClN_3O_3$ M=403.91 g/mol Quantity: 10 mg (yield: 21%) HPLC: t=2.61 min MS: 404.50 (MH⁺) HPLC purity: 96%

3-[4-(2-methylphenyl)piperazino]propyl-N-(2-methoxyphenyl)carbamate 76

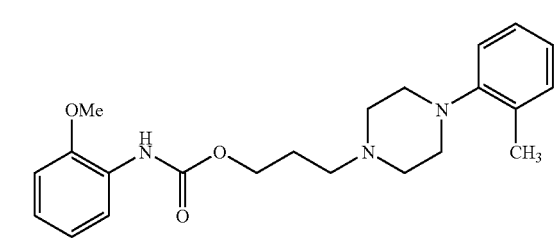

$C_{22}H_{29}N_3O_3$ M=383.49 g/mol Quantity: 8.8 mg (yield: 19%) HPLC: t=2.70 min MS: 384.55 (MH⁺) HPLC purity: 79%

3-[4-(3-methylphenyl)piperazino]propyl-N-(2-methoxyphenyl)carbamate 77

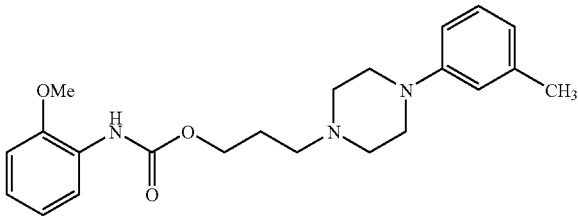

$C_{22}H_{29}N_3O_3$ M=383.49 g/mol Quantity: 9.9 mg (yield: 22%) HPLC: t=2.59 min MS: 384.55 (MH⁺) HPLC purity: 97%

3-[4-(4-methylphenyl)piperazino]propyl-N-(2-methoxyphenyl)carbamate 78

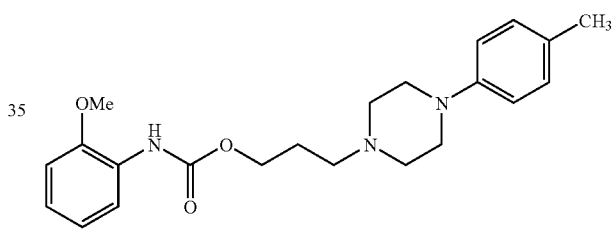

$C_{22}H_{29}N_3O_3$ M=383.49 g/mol Quantity: 13.8 mg (yield: 30%) HPLC: t=2.58 min MS: 384.55 (MH⁺) HPLC purity: 91%

3-[4-(2-fluorophenyl)piperazino]propyl-N-(2-methoxyphenyl)carbamate 79

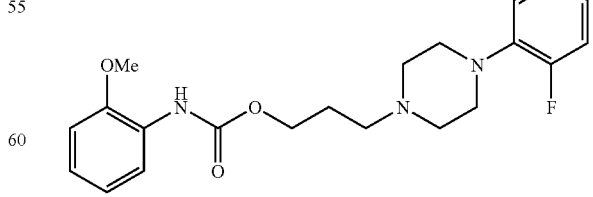

$C_{21}H_{26}FN_3O_3$ M=387.46 g/mol Quantity: 6.3 mg (yield: 14%) HPLC: t=2.55 min MS: 388.52 (MH⁺) HPLC purity: 70%

3-[4-(4-fluorophenyl)piperazino]propyl-N-(2-methoxyphenyl)carbamate 80

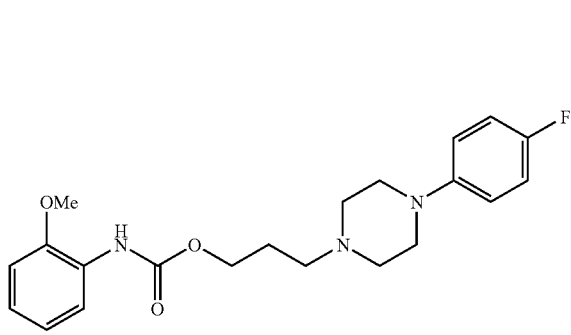

C$_{21}$H$_{26}$FN$_3$O$_3$ M=387.46 g/mol Quantity: 10.1 mg (yield: 22%) HPLC: t=2.50 min MS: 388.53 (MW+) HPLC purity: 92%

3-{4-[3-(trifluoromethyl)phenyl]piperazino}propyl-N-(2-methoxyphenyl)carbamate 81

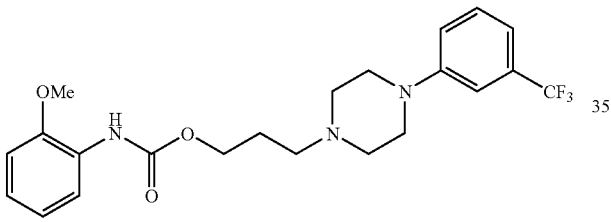

C$_{22}$H$_{26}$F$_3$N$_3$O$_3$ M=437.47 g/mol Quantity: 10.9 mg (yield: 21%) HPLC: t=2.84 min MS: 438.55 (MH$^+$) HPLC purity: 90%

3-[4-(2-pyridinyl)piperazino]propyl-N-(2-methoxyphenyl)carbamate 82

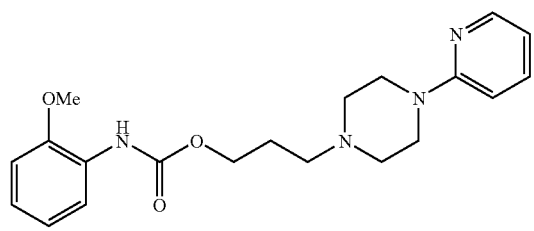

C$_{22}$H$_{26}$N$_4$O$_3$ M=370.46 g/mol Quantity: 9.5 mg (yield: 22%) HPLC: t=2.03 min MS: 371.53 (MH$^+$) HPLC purity: 89%

3-[4-(4-pyridinyl)piperazino]propyl-N-(2-methoxyphenyl)carbamate 83

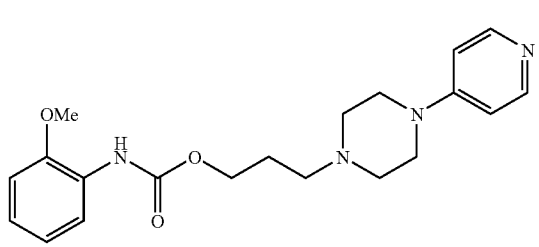

C$_{22}$H$_{26}$N$_4$O$_3$ M=370.46 g/mol Quantity: 4.4 mg (yield: 10%)
RPLC: t=2.11 min MS: 371.52 (MH$^+$) HPLC purity: 76%

3-[2-(4-benzylpiperazino)]propyl-N-(2-methoxyphenyl)carbamate 84

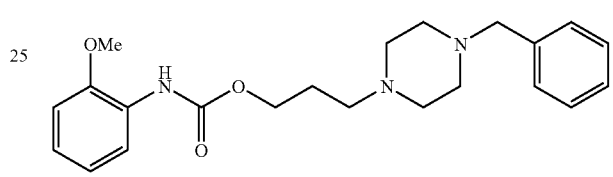

C$_{22}$H$_{29}$N$_3$O$_3$ M=383.49 g/mol Quantity: 7.3 mg (yield: 16%) HPLC: t=2.61 min MS: 384.55 (MH$^+$) HPLC purity: 100%

3-[4-(3-pyridazinyl)piperazino]propyl-N-(2-methoxyphenyl)carbamate 85

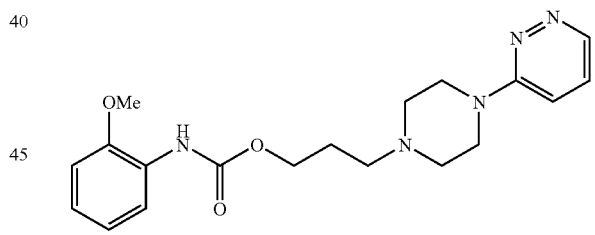

C$_{19}$H$_{25}$N$_5$O$_3$ M=371.44 g/mol Quantity: 4.3 mg (yield: 9%) HPLC: t=2.07 min MS: 372.51 (MH$^+$) HPLC purity: 88%

3-[4-(2-pyrimidinyl)piperazino]propyl-N-(2-methoxyphenyl)carbamate 86

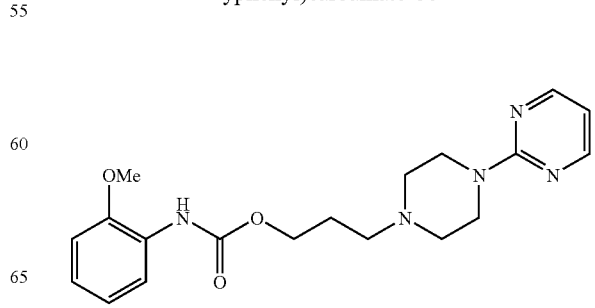

$C_{19}H_{25}N_5O_3$ M=371.44 g/mol Quantity: 3.9 mg (yield: 9%) HPLC: t=2.13 min MS: 372.52 (MH⁺) HPLC purity: 93%

3-[4-(2-pyrazinyl)piperazino]propyl-N-(2-methoxyphenyl)carbamate 87

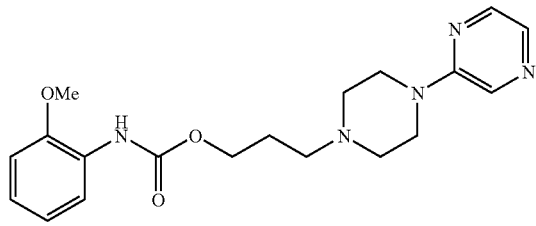

$C_{19}H_{25}N_5O_3$ M=371.44 g/mol Quantity: 4.7 mg (yield: 10%) HPLC: t=2.05 min MS: 372.52 (MH⁺) HPLC purity: 96%

3-[4-(6–Chloro-3-pyridazinyl)piperazino]propyl-N-(2-methoxyphenyl)carbamate 88

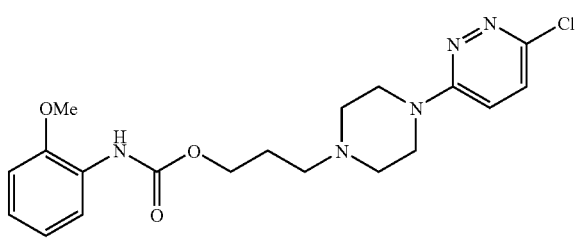

$C_{19}H_{24}ClN_5O_3$ M=371.44 g/mol Quantity: 8.7 mg (yield: 18%) HPLC: t=2.15 min MS: 406.50 (MH⁺) HPLC purity: 95%

3-[4-(2,5-dimethylphenyl)piperazino]propyl-N-(2-methoxyphenyl)carbamate 89

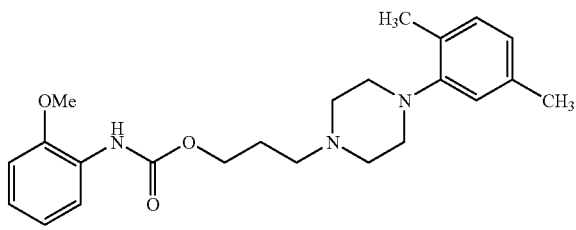

$C_{23}H_{31}N_3O_3$ M=397.52 g/mol Quantity: 6 mg (yield: 13%) HPLC: t=2.85 min MS: 398.58 (MH⁺) HPLC purity: 92%

EXAMPLE 15

2-(4-phenylpiperazino)ethyl-N-(2-ethoxyphenyl)carbamate 90

The reaction between 0.8 g (2.8 mmol) of 2-bromoethyl-N-(2-ethoxyphenyl)carbamate, 1 ml (5.6 mmol, 2 eq) of DIEA and 0.5 ml (3.1 mmol, 1.1 eq) of 1-phenylpiperazine in 7 ml of anhydrous acetonitrile, followed by treatment, according to the procedure described in example 16, yields a yellow oil which is purified by column chromatography (eluent AcOEt/petroleum ether 8:2) to produce 0.47 g of a colorless oil which is stored as the hydrochloride. 485 mg of a white powder is obtained (yield: 39%).

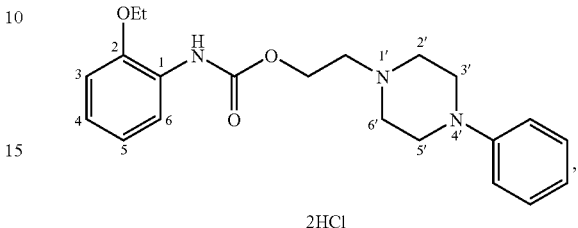

$C_{21}H_{27}N_3O_3 \cdot 2HCl$ M=406.02 g/mol
F=150–154° C.
¹H NMR base (CDCl₃) δ (ppm): 8.10 (dd, $J_o$=6 Hz, $J_m$=3 Hz, 1H, $CH_{(6)}$); 7.34–7.22 (m, 3H, $CH_{(3)}$, $CH_{(4)}$, $CH_{(5)}$); 7.01–6.82 (m, 6H, NH, ArH); 4.35 (t, J=6 Hz, 2H, $CH_2O$); 4.07 (q, J=7 Hz, 2H, $OCH_2$); 3.25–3.20 (m, 4H, $CH_{2(3')}$, $CH_{2(5')}$); 2.78–2.67 (m, 6H, $CH_2N$, $CH_{2(2')}$, $CH_{2(6')}$); 1.43 (t, J=7 Hz, 2H, $CH_3$).

| Elemental analysis: | | |
|---|---|---|
| | Calc. (0.3 H₂O) | Exp. |
| % C | 56.25 | 56.28 |
| % H | 6.66 | 6.66 |
| % N | 9.37 | 9.14 |

EXAMPLE 16

Biological Results

The compounds of the invention were evaluated by measuring their affinity constant Ki determined by displacing a radioligand [³H]-GR113808 in rat glial cells stably expressing the human isoform h5-$HT_{4e}$.

Confluent glial cells were washed twice in PBS and centrifuged at 300 g for 5 min. The pellet was used immediately and the cells were suspended in 10 volumes of HEPES (50 mM, pH 7.4, 4° C.) then homogenized with a teflon homogenizer and centrifuged at 40,000 g for 20 min. The pellet was resuspended in 15 volumes of HEPES. Displacement experiments were carried out in 500 μl of buffer (50 mM HEPES) containing 20 μl of radioligand [³H]-GR113808 at a concentration of 0.2 nM for isoform h5-$HT_{4e}$ or at a concentration equal to half of the Kd of the radioligand for the other isoforms expressed in COS cells, 20 μl of competitor ligand at seven different concentrations and 50 μl of membrane preparation (100–200 μg of protein determined by the Bradford method). Binding was carried out at 25° C. for 30 min and the reaction was stopped by rapid vacuum filtration (Brandel Harvester) on Whatman GF/B filters preincubated in 0.1% PEI solution to minimize nonspecific binding.

Membrane-bound radioactivity is retained on the filter, which was cut and washed with cold buffer (50 mM Tris-HCl, pH 7.4) and incubated overnight in 4 ml of scintillation liquid. Radioactivity was measured in a liquid scintillation counter (Beckman LS 6500C). Binding data were obtained by computer assisted linear regression (Graph Prism Program, Graph Pad Software. Inc., San Diego, Calif.)

The results in the following table are given as an example:

| Compound | Ki (nM) |
|---|---|
| 21 | 20.2 |
| 24 | 4.5 |
| 40 | 9.9 |
| 42 | 3.6 |
| 43 | 10.4 |
| 44 | 11.8 |
| 48 | 3.9 |
| 51 | 12.7 |
| 62 | 9.3 |
| 64 | 10.6 |
| 65 | 10.4 |
| 83 | 10 |

EXAMPLE 17

Preparation of a Library of Molecules Derived from 2-ethoxyaniline

5 μl of TEA (0.033 mmol, 1.1 eq) is added then 500 μl of piperazine (0.03 mmol, 1 eq) dissolved in DMF to 300 μl of 0.2 M 2-bromoethyl-N-(2-ethoxyphenyl)carbamate (0.06 mmol, 2 eq) dissolved in DMF. After 18 hours at room temperature and evaporation of the solvents, the mixtures are taken up in 1 ml of $CH_2Cl_2$ and treated with isocyanate resin (Argonaut, 1.51 mmol/g, 0.09 mmol/g, 0.09 mmol, 3 eq) for 18 hours. Next, the mixtures are purified on cation exchange resins according to the protocol described hereinabove. The desired compounds are then obtained after elimination of the solvents.

The compounds in examples 91 to 118 were obtained by the above method. In this table, "Qty" denotes quantity and RT denotes "retention time".

| No. | Structure | MW | Qty (mg) | Purity % | RT. (min) | m | Ion |
|---|---|---|---|---|---|---|---|
| 91 | 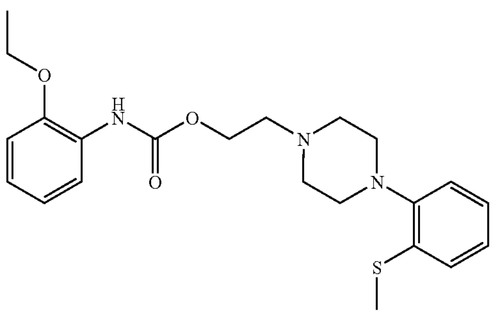 | 415.56 | 2 | 90 | 1.87 | 416.18 | M + 1 |
| 92 | 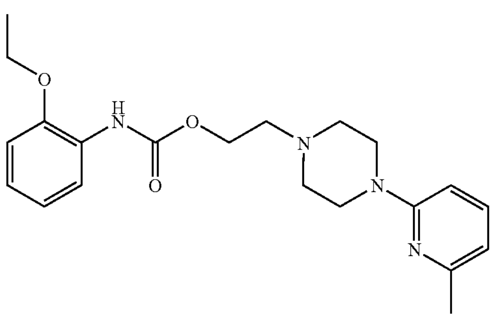 | 384.48 | 1.9 | 95 | 1.4 | 385.09 | M + 1 |
| 93 | 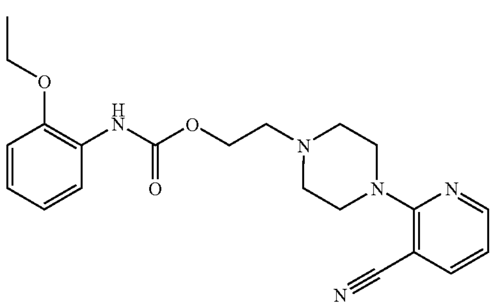 | 395.46 | 2.1 | 69 | 1.67 | 396.1 | M + 1 |

-continued

| No. | Structure | MW | Qty (mg) | Purity % | RT. (min) | m | Ion |
|---|---|---|---|---|---|---|---|
| 94 | 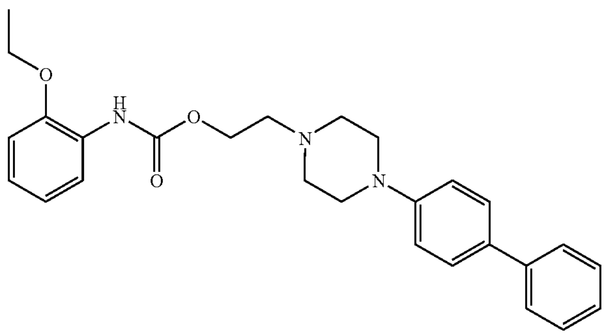 | 445.56 | 1.3 | 73 | 2.05 | 446.25 | M + 1 |
| 95 | 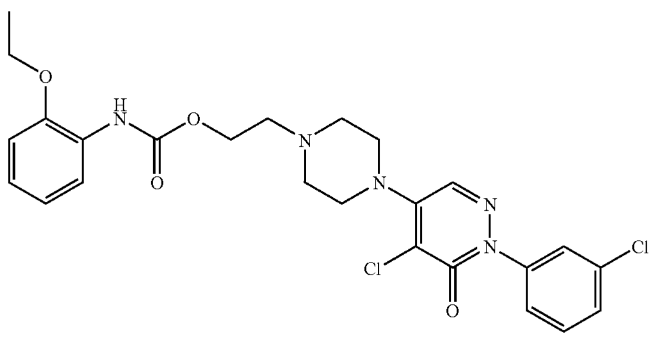 | 532.43 | 1.9 | 92 | 1.83 | 532.17 | M + 1 |
| 96 | 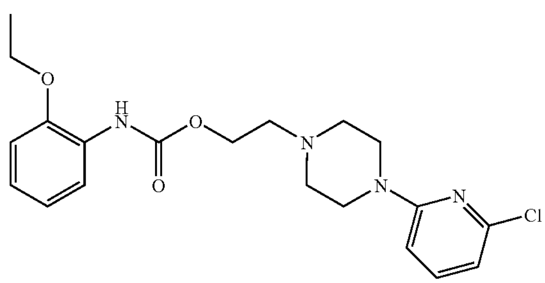 | 404.90 | 2 | 94 | 1.83 | 405.11 | M + 1 |
| 97 | 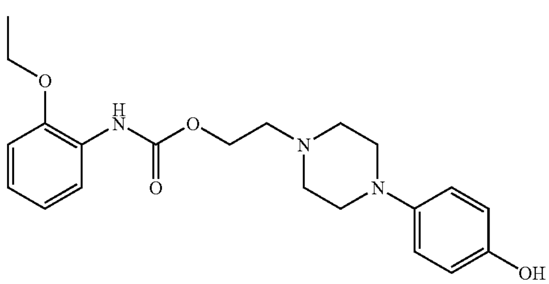 | 385.46 | 3.1 | 100 | 1.57 | 386.12 | M + 1 |
| 98 | 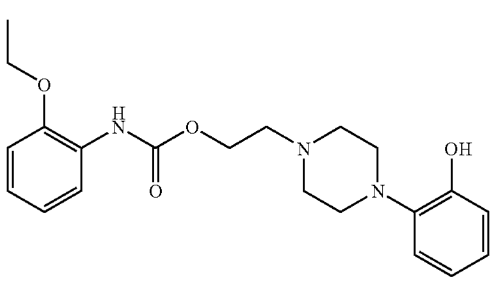 | 385.46 | 2.2 | 93 | 1.69 | 386.12 | M + 1 |

-continued
| No. | Structure | MW | Qty (mg) | Purity % | RT. (min) | m | Ion |
|---|---|---|---|---|---|---|---|
| 99 | 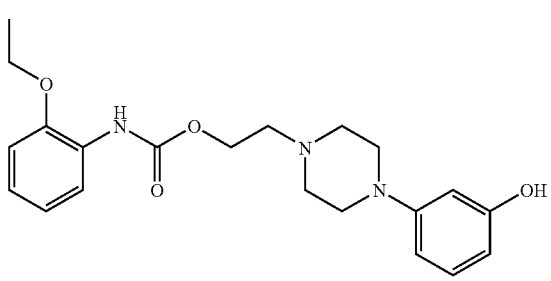 | 385.46 | 1.5 | 81 | 1.64 | 386.11 | M + 1 |
| 100 | 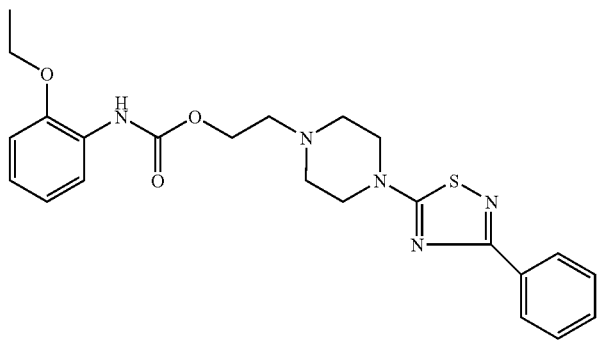 | 453.56 | 2 | 85 | 1.91 | 454.19 | M + 1 |
| 101 | 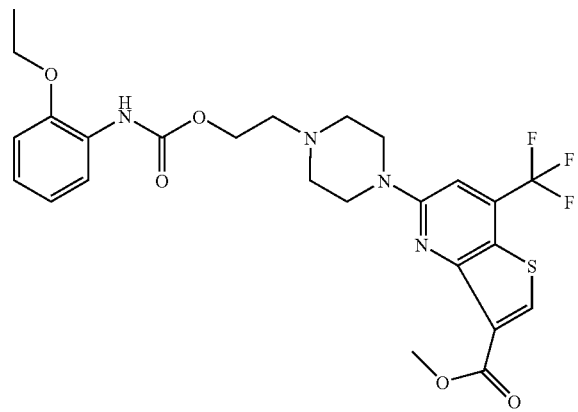 | 552.57 | 2.6 | 87 | 1.99 | 553.18 | M + 1 |
| 102 | 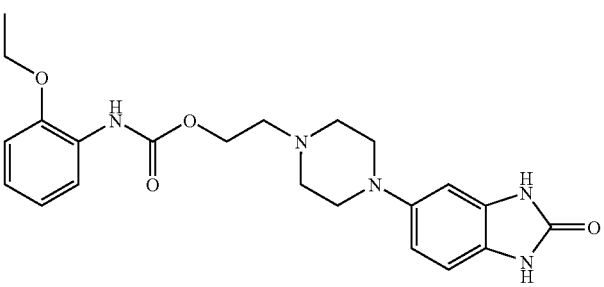 | 425.49 | 1.1 | 100 | 1.52 | 426.18 | M + 1 |

-continued

| No. | Structure | MW | Qty (mg) | Purity % | RT. (min) | m | Ion |
|---|---|---|---|---|---|---|---|
| 103 | 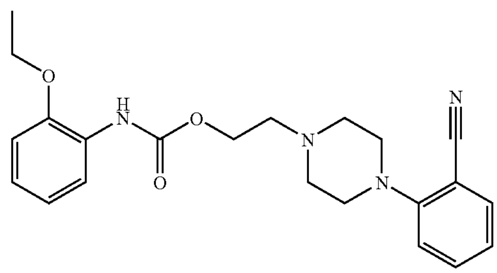 | 394.47 | 2.1 | 93 | 1.76 | 395.11 | M + 1 |
| 104 | 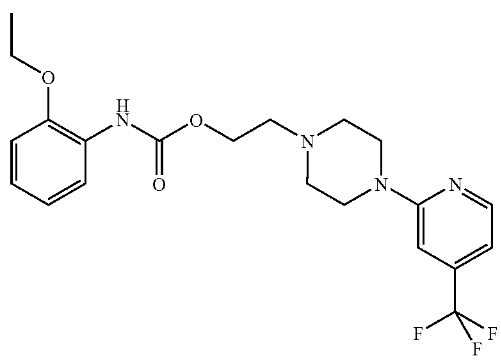 | 438.45 | 2.9 | 83 | 1.87 | 439.21 | M + 1 |
| 105 | 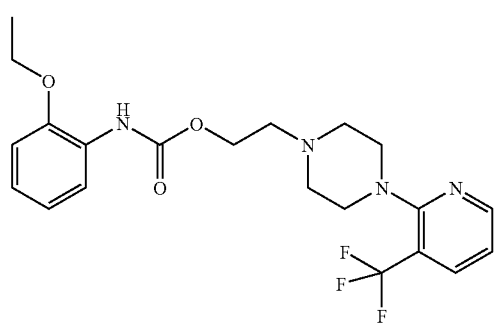 | 438.45 | 2.4 | 97 | 1.8 | 439.24 | M + 1 |
| 106 | 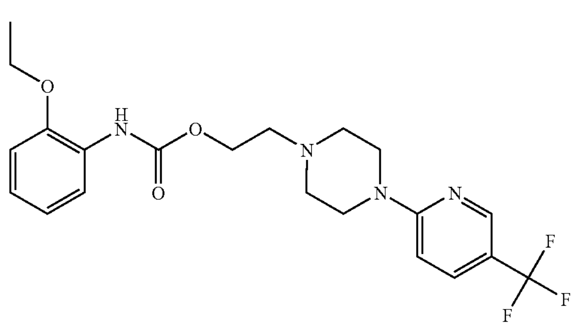 | 438.45 | 2.4 | 86 | 1.88 | 439.22 | M + 1 |

-continued

| No. | Structure | MW | Qty (mg) | Purity % | RT. (min) | m | Ion |
|---|---|---|---|---|---|---|---|
| 107 | 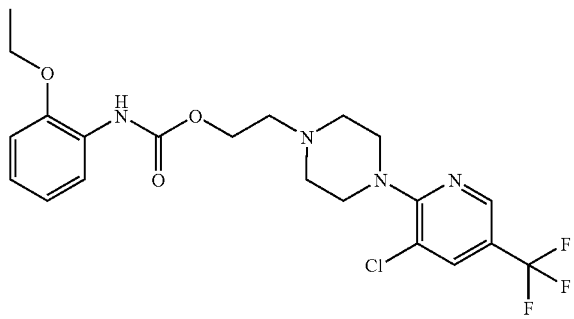 | 472.89 | 2.3 | 94 | 1.95 | 473.11 | M + 1 |
| 108 | 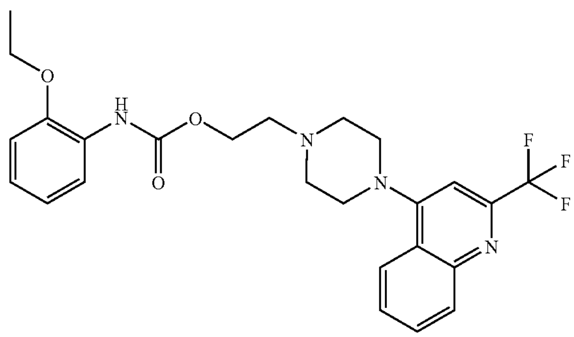 | 488.51 | 2.7 | 83 | 1.91 | 489.17 | M + 1 |
| 109 | 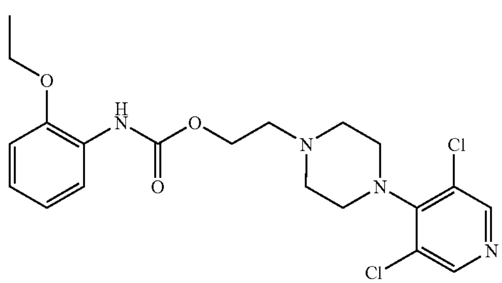 | 438.50 | 2.6 | 88 | 1.69 | 439.16 | M + 1 |
| 110 | 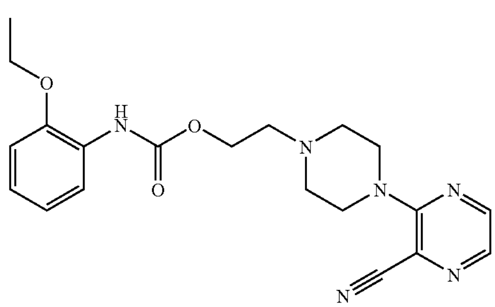 | 396.45 | 2 | 91 | 1.65 | 397.17 | M + 1 |

-continued

| No. | Structure | MW | Qty (mg) | Purity % | RT. (min) | m | Ion |
|---|---|---|---|---|---|---|---|
| 111 | 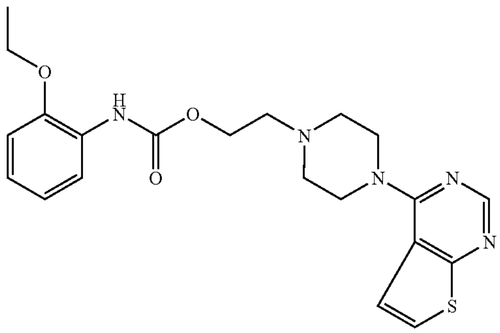 | 427.53 | 2.5 | 81 | 1.59 | 428.19 | M + 1 |
| 112 | 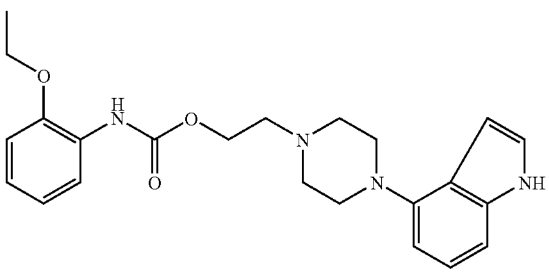 | 408.50 | 2.7 | 82 | 1.74 | 409.2 | M + 1 |
| 113 | 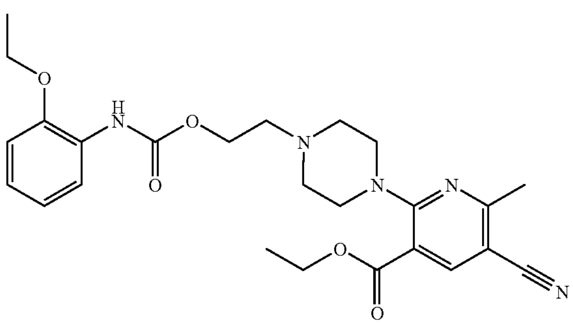 | 481.55 | 2.4 | 91 | 1.87 | 482.19 | M + 1 |
| 114 | 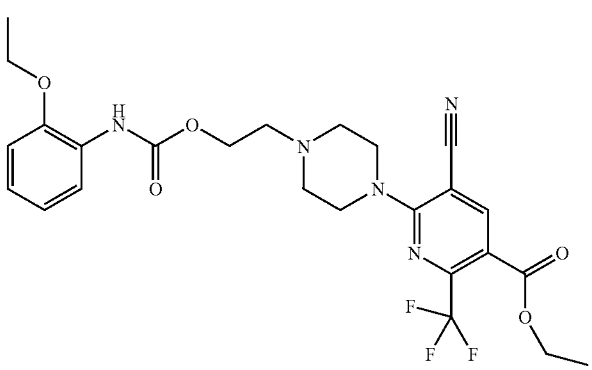 | 535.52 | 2.5 | 89 | 2.01 | 536.25 | M + 1 |

-continued

| No. | Structure | MW | Qty (mg) | Purity % | RT. (min) | m | Ion |
|---|---|---|---|---|---|---|---|
| 115 | 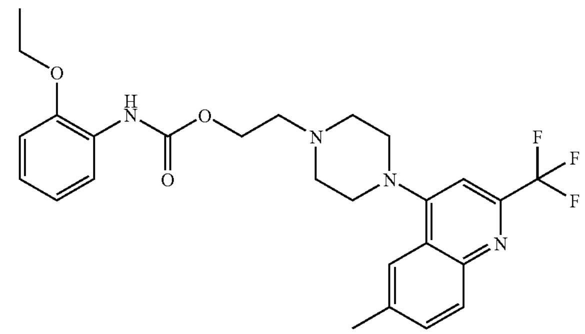 | 502.54 | 3 | 80 | 1.97 | 503.2 | M + 1 |
| 116 | 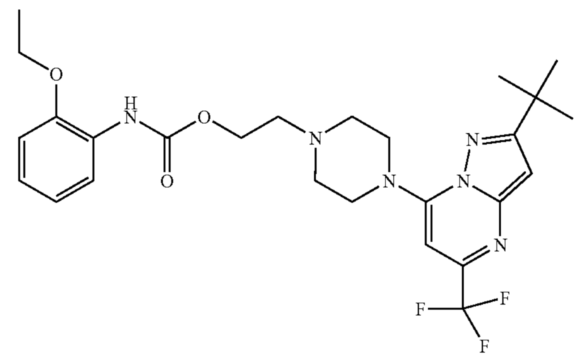 | 534.58 | 2.5 | 82 | 2.11 | 535.31 | M + 1 |
| 117 | 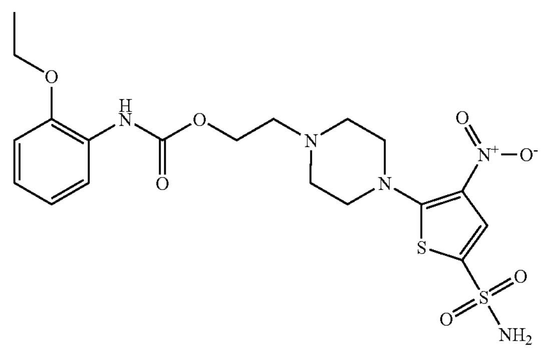 | 499.56 | 1.7 | 68 | 1.65 | 500.1 | M + 1 |
| 118 | 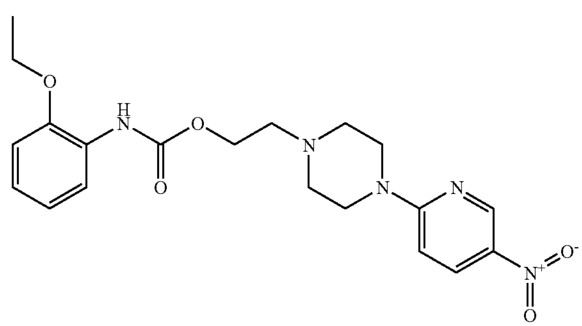 | 415.45 | 1.9 | 82 | 1.73 | 416.17 | M + 1 |

Carbamates Derived from 2-ethoxyaniline 3-piperazinobenzonitrile 6.7 g (77.66 mmol, 5.5 eq) of piperazine are dissolved in 3 ml of DMSO. 1.5 ml (14.12 mmol) of 3-fluorobenzonitrile is added. The mixture is heated at 100° C. for 60 hours. After cooling to room temperature, the reaction mixture is transferred into 126 ml of water. The precipitate formed is filtered and the filtrate extracted with Et₂O. After drying on MgSO₄ and concentration under vacuum, the crude product is purified by column chromatography (eluent CH₂Cl₂/MeOH 9:1) to give 1.39 g of the expected compound in the form of a light yellow oil (yield: 52%).

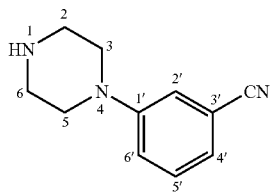

$C_{11}H_{13}N_3$ M=187.27 g/mol $^1$H NMR base (CDCl$_3$) δ (ppm): 7.38–7.28 (m, 1H, ArH); 7.17–7.04 (m, 3H, ArH); 3.24–3.12 (m, 4H, CH$_{2(3)}$, CH$_{2(5)}$); 3.09–2.97 (m, 4H, CH$_{2(2)}$, CH$_{2(6)}$).

2-[4-(3-benzonitrile)piperazino]ethyl-N-(2-ethoxyphenyl)carbamate 119

The reaction between 2.37 g (8.25 mmol) of 2-bromoethyl-N-(2-ethoxyphenyl)carbamate, 1.4 ml (8.25 mmol, 1 eq) of DIEA and 1.4 g (7.42 mmol, 0.9 eq) of 1-(3-benzonitrile)phenylpiperazine and a few KI crystals in 15 ml of DMF, followed by treatment (medium taken up in AcOEt washed with saturated NaCl solution), gives an oil which is purified by column chromatography (eluent AcOEt/petroleum ether 8:2) to produce a mixture which is again purified by column chromatography (eluent CH$_2$Cl$_2$ then CH$_2$Cl$_2$/MeOH 9:1). The product is a colorless oil stored as the hydrochloride. 320 mg of a white powder (yield: 10%) is obtained.

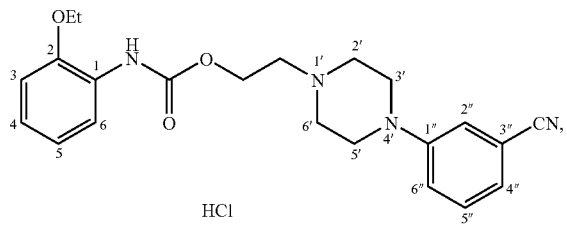

$C_{22}H_{26}N_4O_3$·HCl M=430.94 g/mol $^1$H NMR base (CDCl$_3$) δ (ppm): 8.10 (dd, J$_o$=6 Hz, J$_m$=3 Hz, 1H, CH$_{(6)}$); 7.41–7.22; 7.18–6.76 (m, 8H, NH, ArH); 4.36 (t, J=6 Hz, 2H, OCH$_2$); 4.10 (q, J=7 Hz, 2H, OCH$_2$); 3.33–3.19 (m, 4H, CH$_{2(3')}$, CH$_{2(5')}$); 2.78 (t, J=6 Hz, 2H, CH$_2$N); 2.77–2.64 (m, 4H, CH$_{2(2')}$, CH$_{2(6')}$); 1.45 (t, J=7 Hz, 2H, CH$_3$). $^{13}$C NMR (CD$_3$OD) δ (ppm): 154.6 (CO$_2$); 151.4 (C$_{1''}$); 150.9 (C$_2$); 131.5 (C$_{5''}$); 128.2 (C$_1$); 125.4 (C$_{4''}$); 125.3 (1C, C$_{2''}$–C$_{6''}$); 125.1 (1C, C$_{2''}$–C$_{6''}$); 122.1 (C$_4$); 121.6 (C$_6$); 120.3 (C$_5$); 119.9 (CN); 114.2 (C$_{3''}$); 112.8 (C$_3$); 65.4 (CH$_2$O); 59.6 (CH$_2$O); 57.0 (CH$_2$N); 53.2 (2C, C$_{2'}$, C$_{6'}$); 46.8 (2C, C$_{3'}$, C$_{5'}$); 15.1 (CH$_3$).

| Elemental analysis: | | |
|---|---|---|
| | Calc. (1 H$_2$O) | Exp. |
| % C | 58.85 | 58.79 |
| % H | 6.51 | 6.53 |
| % N | 12.47 | 12.12 |

1-(3-nitrophenyl)piperazine 28.4 g (0.33 mol, 5.5 eq) of piperazine is dissolved in 50 ml of DMSO. 6.4 ml (60 mmol) of 2-fluoronitrobenzene is added. The mixture is heated at 100° C. for 60 hours. After cooling, the reaction mixture is transferred into 530 ml of water. The precipitate formed is filtered and the filtrate extracted with Et$_2$O. After drying on MgSO$_4$ and concentration under vacuum, the crude product is purified by column chromatography (eluent CH$_2$Cl$_2$/MeOH 9:1) to produce 8.04 g of the expected compound in the form of an orange oil which crystallizes at room temperature (yield: 65%).

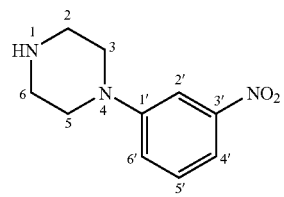

$C_{10}H_{13}N_3O_2$ M=207.26 g/mol $^1$H NMR (CDCl$_3$) δ (ppm): 7.70 (t, J$_m$=2 Hz, 1H, CH$_{(2')}$); 7.64 (ddd, J$_o$=8 Hz, J$_m$=2 Hz, J$_m$=0.6 Hz, 1H, CH$_{(4')}$); 7.36 (t, J$_o$=8 Hz, 1H, CH$_{(5')}$), 7.17 (ddd, J$_o$=8 Hz, J$_m$=2 Hz, J$_m$=0.6 Hz, 1H, CH$_{(6')}$); 3.30–3.18 (m, 4H, CH$_{2(3)}$, CH$_{2(5)}$); 3.09–2.97 (m, 4H, CH$_{2(2)}$, CH$_{2(6)}$).

2-[4-(3-nitrophenyl)piperazino]ethyl-N-(2-ethoxyphenyl)carbamate 120

The reaction between 0.47 g (1.62 mmol) of 2-bromoethyl-N-(2-ethoxyphenyl)carbamate 28, 282 μl (1.62 mmol, 1 eq) of DIEA and 0.42 g (1.46 mmol, 0.9 eq) of 1-(3-nitro)phenylpiperazine and a few KI crystals in 5 ml of DMF, followed by treatment, gives an oil which is purified by column chromatography (eluent AcOEt/petroleum ether 8:2) to produce a mixture which is again purified by column chromatography (eluent CH$_2$Cl$_2$ then CH$_2$Cl$_2$/MeOH 9:1). The product is an orange oil stored as the hydrochloride. One obtains 384 mg of an orange solid (yield: 58%).

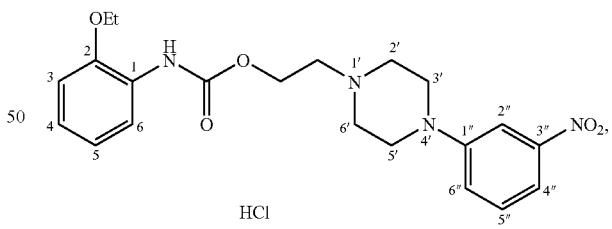

$C_{21}H_{26}N_4O_5$·HCl M=450.93 g/mol $^1$H NMR base (CDCl$_3$) δ (ppm): 8.10 (dd, J$_o$=6 Hz, J$_m$=3 Hz, 1H, CH$_{(6)}$); 7.70 (t, J$_m$=2 Hz, 1H, CH$_{(2'')}$); 7.64 (ddd, J$_o$=8.2 Hz, J$_m$=0.8 Hz, 1H, CH$_{(4'')}$; 7.36 (t, J$_o$=8.2 Hz, 1H, CH$_{(5'')}$), 7.30 (sl, 1H, NH); 7.17 (ddd, J$_o$=8.2 Hz, J$_m$=2 Hz, J$_m$=0.8 Hz, 1H, CH$_{(6'')}$); 7.03–6.80 (m, 3H, CH$_{(3)}$, CH$_{(4)}$, CH$_{(5)}$); 4.35 (t, J=6 Hz, 2H, OCH$_2$); 4.09 (q, J=7 Hz, 2H, OCH$_2$); 3.56–3.26 (m, 4H, CH$_{2(3')}$, CH$_{2(5')}$); 2.77 (t, J=6 Hz, 2H, CH$_2$N); 2.75–2.64 (m, 4H, CH$_{2(2')}$, CH$_{2(6')}$); 1.45 (t, J=7 Hz, 2H, CH$_3$). $^{13}$C NMR base (CDCl$_3$) δ (ppm): 153.2 (CO$_2$); 151.7 (C$_{1''}$); 149.2 (C$_{3''}$); 146.8 (C$_2$); 129.5 (C$_{5''}$); 127.5 (C$_1$); 122.7 (2C, C$_4$, C$_{4''}$); 120.9 (C$_6$); 118.2 (C$_5$); 113.5 (C$_{6''}$); 110.8 (C$_3$);

109.5 (C₂„); 64.0 (CH₂O); 61.9 (CH₂O); 56.9 (CH₂N); 52.9 (2C, C₂', C₆'); 48.2 (2C, C₃', C₅'); 14.8 (CH₃).

| Elemental analysis: | | |
|---|---|---|
| | Calc. (3/4 H₂O) | Exp. |
| % C | 54.30 | 54.31 |
| % H | 6.18 | 6.30 |
| % N | 12.06 | 11.81 |

2-[4-(3-aminophenyl)piperazino]ethyl-N-(2-ethoxyphenyl)carbamate 121

1.08 g (2.60 mmol) of nitro derivative is dissolved in 40 ml of methanol and a spatula tip of Raney nickel is added, placed in a hydrogen atmosphere and shaken at room temperature. The progress of the reaction is monitored by TLC (mobile phase AcOEt/petroleum ether 8:2). After 30 min the reaction mixture becomes decolored. The mixture is then filtered on celite and the filtrate concentrated under reduced pressure. The crude product is taken up in ether, extracted with 1 M HCl. The extracted aqueous phase is then adjusted to alkaline pH by addition of K₂CO₃, then extracted with AcOEt. After drying on Na₂SO₄ and evaporation of the organic phase, 0.8 g of a pure yellow solid is obtained (yield: 80%).

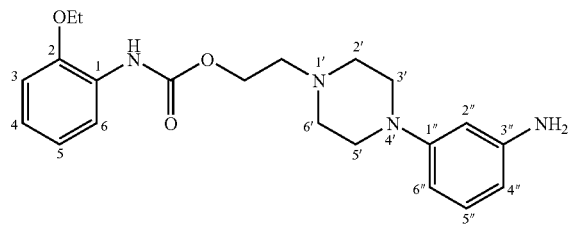

$C_{21}H_{28}N_4O_3$ M=384.53 g/mol ¹H NMR (CDCl₃) δ (ppm): 8.09 (dd, J₀=6 Hz, Jₘ=3 Hz, 1H, CH₍₆₎); 7.31 (sl, 1H, NH); 7.10–6.79 (m, 4H, CH₍₃₎, CH₍₄₎, CH₍₅₎, ArH); 6.39–6.17 (m, 3H, ArH); 4.35 (t, J=6 Hz, 2H, OCH₂); 4.09 (q, J=7 Hz, 2H, OCH₂); 3.59 (sl, 2H, NH₂); 3.25–3.14 (m, 4H, CH₂₍₃'₎, CH₂₍₅'₎); 2.76 (t, J=6 Hz, 2H, CH₂N); 2.70–2.60 (m, 4H, CH₂₍₂'₎, CH₂₍₆'₎); 1.45 (t, J=7 Hz, 2H, CH₃). ¹³C NMR (CDCl₃) δ (ppm): 153.4 (CO₂); 152.5 (C₁„); 147.3 (C₃„); 146.9 (C₂); 129.9 (C₅„); 127.7 (C₁); 122.7 (C₄); 120.9 (C₆); 118.3 (C₅); 110.9 (C₃); 107.0 (C₄„); 106.9 (C₆„); 102.9 (C₂„); 64.0 (CH₂O); 62.0 (CH₂O); 57.0 (CH₂N); 53.4 (2C, C₂', C₆'); 48.8 (2C, C₃', C₅'); 14.8 (CH₃).

| Elemental analysis: | | |
|---|---|---|
| | Calc. (1/4 H₂O) | Exp. |
| % C | 64.84 | 64.93 |
| % H | 7.38 | 7.37 |
| % N | 14.40 | 14.23 |

2-{4-[3-(acetylamino)phenyl]piperazino}ethyl-N-(2-ethoxyphenyl)carbamate 122

To a mixture of 77 mg (0.2 mmol) of 2-[4-(3-aminophenyl)piperazino]ethyl-N-(2-ethoxyphenyl)carbamate derivative and 44.6 μl (0.32 mmol, 1.6 eq) of TEA in 5 ml of THF, 71 μl (0.3 mmol, 1.5 eq) of acetyl chloride is added. Shaking is carried out at room temperature for about 20 hours. Then H₂O is added and the aqueous phase is extracted with CH₂Cl₂. After drying on Na₂SO₄ and concentration under vacuum, a white solid is obtained which is purified by column chromatography (eluent CH₂Cl₂/iPrOH 9:1) to produce 36 mg of the expected product as a brown oil (yield: 43%).

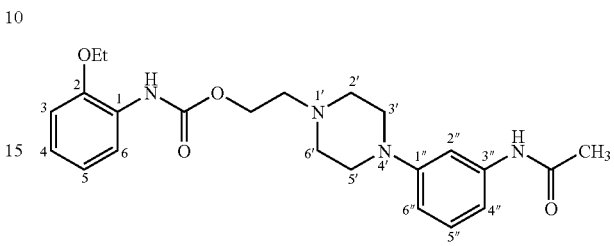

$C_{23}H_{30}N_4O_4$ M=426.51 g/mol ¹H NMR (CDCl₃) δ (ppm): 8.08 (dd, J₀=6 Hz, Jₘ=3 Hz, 1H, CH₍₆₎); 7.41 (sl, 1H, NH); 7.31 (sl, 1H, NH); 7.16 (t, J=8., 2 Hz, 1H, ArH); 7.04–6.79 (m, 5H, ArH); 6.72–6.59 (m, 1H, ArH); 4.34 (t, J=6 Hz, 2H, OCH₂); 4.08 (q, J=7 Hz, 2H, OCH₂); 3.30–3.10 (m, 4H, CH₂₍₃'₎, CH₂₍₅'₎); 2.75 (t, J=6 Hz, 2H, CH₂N); 2.70–2.59 (m, 4H, CH₂₍₂'₎, CH₂₍₆'₎); 2.13 (s, 3H, CH₃); 1.45 (t, J=7 Hz, 2H, CH₃). ¹³C NMR (CDCl₃) δ (ppm): 162.8 (CO); 153.3 (CO₂); 151.8 (C₁„); 146.9 (C₂) 138.8 (C₃„); 129.3 (C₅„); 127.5 (C₁); 122.7 (C₄); 120.8 (C₆); 118.2 (C₅); 111.7 (2C, C₄„, C₆„); 110.8 (C₃); 107.5 (C₂„); 64.0 (CH₂O); 61.9 (CH₂O); 56.9 (CH₂N); 53.2 (2C, C₂', C₆'); 48.6 (2C, C₃', C₅'); 24.5 (CH₃); 14.8 (CH₃). HPLC: t=1.51 min MS: 427.55 (MH⁺) HPLC purity: 100%

2-{4-[3-(methylsulfonylamino)phenyl]piperazino}ethyl-N-(2-ethoxyphenyl)carbamate 123

To a mixture of 77 mg (0.2 mmol) of 2-[4-(3-aminophenyl)piperazino]ethyl-N-(2-ethoxyphenyl)carbamate derivative and 56 μl (0.4 mmol, 2 eq) of TEA in 5 ml of THF, 31 μl (0.4 mmol, 2 eq) of mesyl chloride is added. Shaking is carried out at room temperature for about 20 hours. After concentration under reduced pressure, H₂O is added and the aqueous phase is extracted with CH₂Cl₂. After drying on Na₂SO₄ and concentration of the organic phase, a brown oil is obtained which is purified by column chromatography (eluent AcOEt/petroleum ether 8:2) to produce 61 mg of the expected product as a brown oil (yield: 66%).

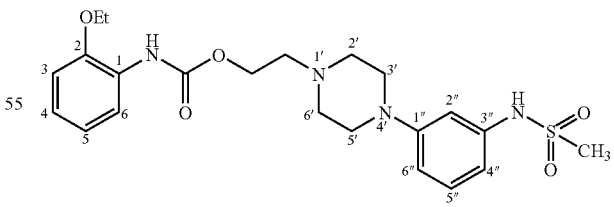

$C_{22}H_{30}N_4SO_5$ M=462.63 g/mol ¹H NMR (CDCl₃) δ (ppm): 8.08 (dd, J₀=6 Hz, Jₘ=3 Hz, 1H, CH₍₆₎); 7.31 (sl, 1H, NH); 7.20 (t, J=8, 2 Hz, 1H, ArH); 7.06–6.58 (m, 6H, ArH); 6.50 (sl, 1H, NH); 4.35 (t, J=6 Hz, 2H, OCH₂); 4.09 (q, J=7 Hz, 2H, OCH₂); 3.34–3.17 (m, 4H, CH₂₍₃'₎, CH₂₍₅'„₎; 2.99 (s, 3H, CH₃); 2.78 (t, 2H CH₂N); 2.70–2.60 (m, 4H, CH₂₍₂'₎, CH₂₍₆'₎); 1.45 (t, J=7 Hz, 2H, CH₃). ¹³C NMR (CDCl₃) δ

(ppm): 156.8 (CO$_2$); 152.3 (C$_{1''}$); 146.9 (C$_2$); 137.8 (C$_{3''}$); 130.1 (C$_{5''}$); 127.6 (C$_1$); 122.7 (C$_4$); 120.9 (C$_6$); 118.3 (C$_5$); 112.8 (1C, C$_{4''}$–C$_{6''}$); 111.3 (1C, C$_{4''}$–C$_{6''}$); 110.9 (C$_3$); 107.8 (C$_{2''}$); 64.1 ($\underline{C}$H$_2$O); 62.0 (CH$_2$O); 57.0 ($\underline{C}$H$_2$N); 53.2 (2C, C$_{2'}$, C$_{6'}$); 48.5 (2C, C$_{3'}$, C$_{5'}$); 39.1 ($\underline{C}$H$_3$); 14.7 ($\underline{C}$H$_3$). HPLC: t=1.55 min MS: 463.49 (MH$^+$) HPLC purity: 93%

2-[4-(3-{[(ethylamino)carbonyl]amino}phenyl)piperazino]ethyl-N-(2-ethoxyphenyl)carbamate 124

Dilute 120 µl (1.5 mmol, 3 éeq) of ethylisocyanate in 5 ml of CH$_2$Cl$_2$. Add 192 mg of 2-[4-(3-aminopheényl)piperazino]ethyl-N-(2-ethoxyphenyl)carbamate dissolved in 5 ml of CH$_2$Cl$_2$ and react under a reflux condenser for 18 hours, then at room temperature for approximately 60 hours. The reaction medium is then concentrated under reduced pressure, taken up in 4 ml of CH$_2$Cl$_2$ and reacted with methylisocyanate resin (0.5 mmol, 1 eq) at room temperature for 24 hours. After filtration of the resin, the filtrate is evaporated to give a yellow oil which crystallizes at room temperature. One obtains 149 mg of the expected pure compound (yield: 65%).

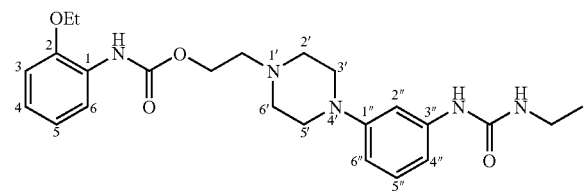

C$_{24}$H$_{33}$N$_5$O$_4$ M=455.62 g/mol $^1$H NMR (CDCl$_3$) δ (ppm): 8.07 (dd, J$_o$=6 Hz, J$_m$=3 Hz, 1H, CH$_{(6)}$); 7.48 (s1, 1H, NH); 7.36 (sl, 1H, NH); 7.30–6.42 (m, 7H, ArH); 5.60 (t, J=5, 3 Hz, 1H, NH); 4.33 (t, J=6 Hz, 2H, OCH$_2$); 4.08 (q, J=7 Hz, 2H, OCH$_2$); 3.33–3.06 (m, 6H, CH$_{2(3')}$, CH$_{2(5')}$, CH$_2$); 2.75 (t, 2H, J=6 Hz CH$_2$N); 2.70–2.54 (m, 4H, CH$_{2(2')}$, CH$_{2(6')}$); 1.44 (t, J=7 Hz, 2H, CH$_3$); 1.09 (t, J=7.2 Hz, 2H, CH$_3$). $^{13}$C NMR (CDCl$_3$) δ (ppm): 156.6 (CO); 153.3 (CO$_2$); 151.6 (C$_{1''}$); 147.0 (C$_2$); 140.3 (C$_{3''}$); 129.3 (C$_{5''}$); 127.4 (C$_1$); 122.9 (C$_4$); 120.8 (C$_6$); 118.3 (C$_5$); 110.9 (2C, C$_{4''}$, C$_{6''}$); 110.0 (C$_3$); 107.2 (C$_{2''}$); 64.0 ($\underline{C}$H$_2$O); 61.7 ($\underline{C}$H$_2$O); 56.8 ($\underline{C}$H$_2$N); 53.1 (2C, C$_{2'}$, C$_{6'}$); 48.4 (2C, C$_{3'}$, C$_{5'}$); 34.7 ($\underline{C}$H$_2$); 15.3 ($\underline{C}$H$_3$); 14.7 ($\underline{C}$H$_3$).

The invention claimed is:

1. A compound represented by the general formula (I):

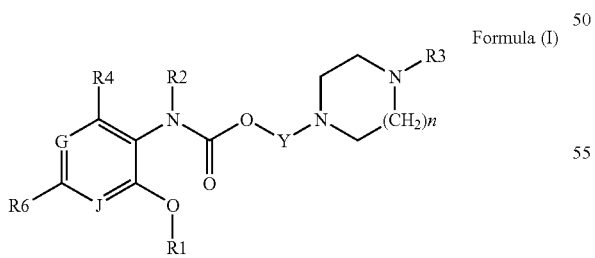

Formula (I)

wherein

R$_1$ represents a lower alkyl group,

R$_2$ represents the hydrogen atom,

R$_3$ represents a heterocycle, chosen from among, pyrimidinyl, pyridazinyl or pyrazinyl, such group optionally being substituted by one or more groups chosen from among halogeno, cyano, nitro, alkyl or halogenoalkyl, Y represents an alkylene bond or chain, linear or branched, having 2 or 3 to 5carbon atoms, J represents a C—R$_7$ group, G represents a C—R$_5$ group, R$_4$, R$_5$, R$_6$ and R$_7$ represent the hydrogen atom, n is equal to 1, and the salts thereof.

2. A compound represented by the general formula (I) according to claim 1, wherein R$_1$ represents a methyl or ethyl group.

3. A compound chosen from among: 2-[4-(2-pyridinyl)piperazino]ethyl-N-(2-ethoxyphenyl)carbamate 2-[4-(3-pyridazinyl)piperazino]ethyl-N-(2-ethoxyphenyl)carbamate 3-[4-(2-pyridinyl)piperazino]propyl-N-(2-ethoxyphenyl)carbamate 3-[4-(4-pyridinyl)piperazino]propyl-N-(2-ethoxyphenyl)carbamate 3-[4-(3-pyridazinyl)piperazino]propyl-N-(2-ethoxyphenyl)carbamate 3-[4-(4-pyrimidinyl)piperazino]propyl-N-(2-ethoxyphenyl)carbamate 3-[4-(2-pyrimidinyl)piperazino]propyl-N-(2-ethoxyphenyl)carbamate 3-[4-(6-methyl-3-pyridazinyl)piperazino]propyl-N-(2-ethoxyphenyl)carbamate 2-[4-(2-pyridinyl)piperazino]ethyl-N-(2-methoxyphenyl)carbamate 2-[4-(3-pyridazinyl)piperazino]ethyl-N-(2-methoxyphenyl)carbamate 2-[4-(2-pyrimidinyl)piperazino]ethyl-N-(2-methoxyphenyl)carbamate 3-[4-(4-pyridinyl)piperazino]propyl-N-(2-methoxyphenyl)carbamate and the salts thereof.

4. A pharmaceutical composition comprising a compound according to claim 1 or claim 3.

5. A method of treatment of urinary incontinence, comprising administering to a subject, particularly human, an effective dose of a compound as defined in claim 1.

6. A method for preparing a compound according to claim 1, wherein a compound represented by formula (II) is reacted with a compound represented by formula (III):

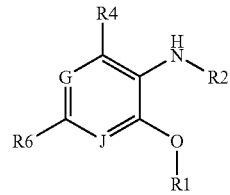

(II)

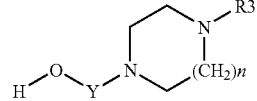

(III)

in which the groups R$_1$, R$_2$, R$_3$, R$_4$, R$_6$, Y, J, G and n are defined as in claim 1, in the presence of a carbonyl donor reagent and the resulting product is recovered.

7. A method according to claim 6, wherein said carbonyl donor reagent is the (Boc)$_2$O/DMAP system.

8. A method according to claim 6, wherein a compound represented by formula (II) is reacted with a compound represented by formula (III), in a CXCl$_2$/pyridine system, and the resulting compound is recovered.

* * * * *